(12) United States Patent
Itami et al.

(10) Patent No.: US 8,993,777 B2
(45) Date of Patent: Mar. 31, 2015

(54) METHOD FOR PRODUCING PHENYL-SUBSTITUTED HETEROCYCLIC DERIVATIVE

(71) Applicant: National University Corporation Nagoya University, Nagoya-shi (JP)

(72) Inventors: Kenichiro Itami, Nagoya (JP); Junichiro Yamaguchi, Nagoya (JP); Kei Muto, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 14/355,035

(22) PCT Filed: Oct. 10, 2012

(86) PCT No.: PCT/JP2012/076242
§ 371 (c)(1),
(2) Date: Apr. 29, 2014

(87) PCT Pub. No.: WO2013/065463
PCT Pub. Date: May 10, 2013

(65) Prior Publication Data
US 2014/0275549 A1 Sep. 18, 2014

(30) Foreign Application Priority Data

Oct. 31, 2011 (JP) .................................. 2011-239604

(51) Int. Cl.
| | | |
|---|---|---|
| *C07D 263/30* | (2006.01) | |
| *C07D 277/20* | (2006.01) | |
| *C07D 277/60* | (2006.01) | |
| *C07D 263/56* | (2006.01) | |
| *C07D 263/34* | (2006.01) | |
| *C07D 263/57* | (2006.01) | |
| *C07D 413/04* | (2006.01) | |
| *C07D 263/32* | (2006.01) | |
| *C07D 277/22* | (2006.01) | |
| *C07D 277/66* | (2006.01) | |
| *C07D 471/08* | (2006.01) | |

(52) U.S. Cl.
CPC ............ *C07D 263/57* (2013.01); *C07D 263/56* (2013.01); *C07D 413/04* (2013.01); *C07D 263/32* (2013.01); *C07D 263/34* (2013.01); *C07D 277/22* (2013.01); *C07D 277/66* (2013.01); *C07D 471/08* (2013.01)
USPC ........... 548/235; 548/202; 548/152; 548/224; 548/236

(58) Field of Classification Search
CPC .................................................... C07D 263/32
USPC .......... 548/235, 236, 202, 152, 224
See application file for complete search history.

(56) References Cited

PUBLICATIONS

Canivet et al. (Organic Letters (2009), 11(8), 1733-1736).*
English translation of the International Search Report issued Nov. 6, 2012, in PCT/JP2012/076242.
Takuya Yamamoto, et al., "Nickel-Catalyzed C—H Arylation of Azoles with Haloarenes: Scope, Mechanism, and Applications to the Synthesis of Bioactive Molecules", Chem. Eur. J., vol. 17, Jul. 8, 2011, pp. 10113-10122.
Jérôme Cavinet, et al., "Nickel-Catalyzed Biaryl Coupling of Heteroarenes and Aryl Halides/Triflates", Organic Letters, vol. 11, No. 8, 2009, pp. 1733-1736.
Julien Roger, et al., "Aryl triflates: useful coupling partners for the direct arylation of heteroaryl derivatives via Pd-catalyzed C—H activation functionalization", Organic & Biomolecular Chemistry, vol. 6, 2008, pp. 169-174.
Neil A. Strotman, et al., "Highly Regioselective Palladium-Catalyzed Direct Arylation of Oxazole at C-2 or C-5 with Aryl Bromides, Chlorides, and Triflates", Organic Letters., vol. 12, No. 16, 2010, pp. 3578-3581.
Fengzhi Zhang, et al., "Decarboxylative C—H Cross-Coupling of Azoles", Angew. Chem. Int. Ed., vol. 49, 2010, pp. 2768-2771.
Kei Muto, et al, "Nickel-Catalyzed C—H/C—O Coupling of Azoles with Phenol Derivatives", Journal of the American Chemical Society, vol. 134, Dec. 8, 2011, pp. 169-172.
European Search Report as received in the corresponding European Patent Application No. 12845027.7 dated Nov. 27, 2014.

* cited by examiner

*Primary Examiner* — Nizal Chandrakumar
(74) *Attorney, Agent, or Firm* — Oblon, McClelland, Maier & Neustadt, L.L.P.

(57) ABSTRACT

The present invention is a method for producing a phenyl-substituted heterocyclic derivative represented by general formula (1), which has a step wherein a heteroaromatic compound represented by general formula (2) is reacted with a phenol derivative represented by general formula (3) in the presence of a nickel compound, 1,2-bis(dicyclohexylphosphino)ethane, and a base.

9 Claims, No Drawings

METHOD FOR PRODUCING PHENYL-SUBSTITUTED HETEROCYCLIC DERIVATIVE

CROSS REFERENCE TO RELATED APPLICATIONS

The present application is a 35 U.S.C. §371 national stage patent application of International patent application PCT/JP2012/076242, filed on Oct. 10, 2012, published as WO/2013/065463 on May 10, 2013, the text of which is incorporated by reference, and claims the benefit of the filing date of Japanese application no. 2011-239604, filed on Oct. 31, 2011, the text of which is also incorporated by reference.

TECHNICAL FIELD

The present invention relates to a method for producing a phenyl-substituted heterocyclic derivative.

BACKGROUND ART

A phenyl-substituted heterocyclic derivative is useful in a wide range of applications (e.g., as an antipodagric or a drug for treating amyloid polyneuropathy). An arylation reaction that arylates a C—H bond of an aromatic ring has attracted attention as an ideal biaryl skeleton-forming technique, and extensive studies have been conducted to further improve the reaction system.

It has been known that a C—H/C—X coupling reaction between an azole and an aryl halide proceeds in the presence of an Ni(OAc)$_2$/bipy catalyst and LiOt-Bu or Mg(Ot-Bu)$_2$ (additive) (see Non-Patent Documents 1 and 2).

An organoboron compound and an organosilicon compound have been known as a raw material that is reacted with an azole.

PRIOR TECHNICAL DOCUMENT

Patent Document

Non-Patent Document 1: Org. Lett. 11, 2009, 1733
Non-Patent Document 2: Chem. Eur. J. 17, 2011, 10113

SUMMARY OF THE INVENTION

Technical Problem

However, the above technique has the following problems.
(a) An aryl halide may not be easily available, and an organoboron compound and an organosilicon compound are normally synthesized from an aryl halide.
(b) The atom efficiency of the entire synthesis process is poor (i.e., it is necessary to dispose of a salt produced as a by-product, and the weight ratio thereof is high).
(c) An aryl halide, an organoboron compound, and an organosilicon compound may undergo a side reaction due to high chemical reactivity.
(d) It has been desired not to use a halogen from the viewpoint of reducing environmental impact.

An object of the present invention is to provide a method that can produce a phenyl-substituted heterocyclic derivative without using an aryl halide, and can suppress environmental impact.

Means for Solving the Problems

The inventors conducted extensive studies, and found that a phenyl-substituted heterocyclic derivative can be obtained through a coupling reaction by utilizing a specific phenol derivative, a specific heteroaromatic compound, a nickel-based catalyst, and 1,2-bis(dicyclohexylphosphino)ethane (bidentate ligand) in combination.

The present invention is a production method of a phenyl-substituted heterocyclic derivative that is represented by the following general formula (1) and is characterized in that the method includes a step of reacting a heteroaromatic compound represented by the following general formula (2) with a phenol derivative represented by the following general formula (3) in the presence of a nickel compound, 1,2-bis(dicyclohexylphosphino)ethane, and a base.

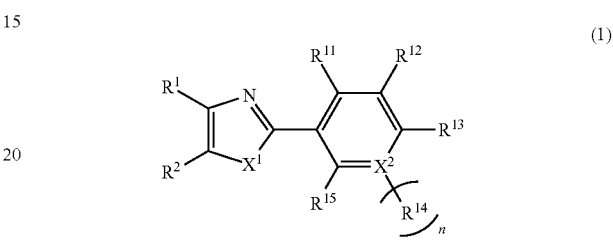

(1)

(In the formula, $X^1$ is an oxygen atom or a sulfur atom, $X^2$ is a carbon atom or a nitrogen atom, n is 0 when $X^2$ is a nitrogen atom, and is 1 when $X^2$ is a carbon atom, $R^1$ is a hydrogen atom, a hydrocarbon group having 1 to 20 carbon atoms, a group derived therefrom, or an ester group, $R^2$ is a hydrogen atom, a hydrocarbon group having 1 to 20 carbon atoms, a group derived therefrom, or an ester group, provided that $R^1$ and $R^2$ optionally bond to each other to form a divalent organic group having 4 to 6 carbon atoms, $R^{11}$ is a hydrogen atom, a hydrocarbon group having 1 to 20 carbon atoms, a group derived therefrom, or an alkoxy group having 1 to 10 carbon atoms, $R^{12}$ is a hydrogen atom, a hydrocarbon group having 1 to 20 carbon atoms, a group derived therefrom, or an alkoxy group having 1 to 10 carbon atoms, $R^{13}$ is a hydrogen atom, a hydrocarbon group having 1 to 20 carbon atoms, a group derived therefrom, or an alkoxy group having 1 to 10 carbon atoms, $R^{14}$ is a hydrogen atom, a hydrocarbon group having 1 to 20 carbon atoms, a group derived therefrom, or an alkoxy group having 1 to 10 carbon atoms, and $R^{15}$ is a hydrogen atom, a hydrocarbon group having 1 to 20 carbon atoms, a group derived therefrom, or an alkoxy group having 1 to 10 carbon atoms, provided that $R^{11}$ and $R^{12}$ optionally bond to each other to form a divalent organic group having 4 to 6 carbon atoms, $R^{12}$ and $R^{13}$ optionally bond to each other to form a divalent organic group having 4 to 6 carbon atoms, $R^{13}$ and $R^{14}$ optionally bond to each other to form a divalent organic group having 4 to 6 carbon atoms, and $R^{14}$ and $R^{15}$ optionally bond to each other to form a divalent organic group having 4 to 6 carbon atoms.)

(2)

(In the formula, $X^1$ is an oxygen atom or a sulfur atom, $R^1$ is a hydrogen atom, a hydrocarbon group having 1 to 20 carbon atoms, a group derived therefrom, or an ester group, $R^2$ is a hydrogen atom, a hydrocarbon group having 1 to 20 carbon atoms, a group derived therefrom, or an ester group, provided that $R^1$ and $R^2$ optionally bond to each other to form a divalent organic group having 4 to 6 carbon atoms.)

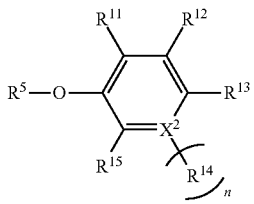

(3)

(In the formula, $X^2$ is a carbon atom or a nitrogen atom, n is 0 when $X^2$ is a nitrogen atom, and is 1 when $X^2$ is a carbon atom, $R^5$ is an acyl group, a dialkylcarbamoyl group, an alkyl carbonate group, an aryl carbonate group, an aralkyl carbonate group, a triflate group, an alkylsulfonyl group, an arylsulfonyl group, an aralkylsulfonyl group, a dialkylsulfamoyl group, or a diarylsulfamoyl group, $R^{11}$ is a hydrogen atom, a hydrocarbon group having 1 to 20 carbon atoms, a group derived therefrom, or an alkoxy group having 1 to 10 carbon atoms, $R^{12}$ is a hydrogen atom, a hydrocarbon group having 1 to 20 carbon atoms, a group derived therefrom, or an alkoxy group having 1 to 10 carbon atoms, $R^{13}$ is a hydrogen atom, a hydrocarbon group having 1 to 20 carbon atoms, a group derived therefrom, or an alkoxy group having 1 to 10 carbon atoms, $R^{14}$ is a hydrogen atom, a hydrocarbon group having 1 to 20 carbon atoms, a group derived therefrom, or an alkoxy group having 1 to 10 carbon atoms, and $R^{15}$ is a hydrogen atom, a hydrocarbon group having 1 to 20 carbon atoms, a group derived therefrom, or an alkoxy group having 1 to 10 carbon atoms, provided that $R^{11}$ and $R^{12}$ optionally bond to each other to form a divalent organic group having 4 to 6 carbon atoms, $R^{12}$ and $R^{13}$ optionally bond to each other to form a divalent organic group having 4 to 6 carbon atoms, $R^{13}$ and $R^{14}$ optionally bond to each other to form a divalent organic group having 4 to 6 carbon atoms, and $R^{14}$ and $R^{15}$ optionally bond to each other to form a divalent organic group having 4 to 6 carbon atoms.)

Effects of the Invention

According to the present invention, it is possible to produce the heterocyclic compound represented by the general formula (1) using the phenol derivative represented by the general formula (3) as the reaction raw material without using an aryl halide. While a side reaction may occur when using an aryl halide (i.e., arylating agent) due to high chemical reactivity, the method according to the present invention can eliminate a side reaction, or suppress a side reaction to a large extent. Since the raw material that replaces an aryl halide is used, it is possible to suppress environmental impact. When using an aryl halide, a metal compound (e.g., Li compound or Mg compound) is used as an additive. In this case, it is necessary to dispose of a large amount of metal salts (Li salts or Mg salts) (by-products) (i.e., the atom efficiency decreases). Since a carboxylic acid or carbamic acid is disposed of when using the method according to the present invention, the weight of waste can be reduced, and a high atom efficiency can be achieved.

EMBODIMENTS FOR CARRYING OUT THE INVENTION

The production method of the present invention includes a step of reacting the heteroaromatic compound represented by the general formula (2) with the phenol derivative represented by the general formula (3) in the presence of the nickel compound, 1,2-bis(dicyclohexylphosphino)ethane, and the base (hereinafter referred to as "reaction step"). The reaction scheme is shown below.

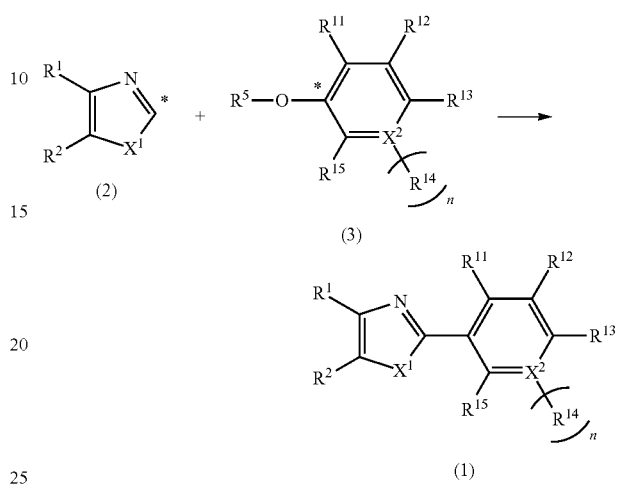

(In the formula, $X^1$ is an oxygen atom or a sulfur atom, $R^1$ is a hydrogen atom, a hydrocarbon group having 1 to 20 carbon atoms, a group derived therefrom, or an ester group, $R^2$ is a hydrogen atom, a hydrocarbon group having 1 to 20 carbon atoms, a group derived therefrom, or an ester group, provided that $R^1$ and $R^2$ optionally bond to each other to form a divalent organic group having 4 to 6 carbon atoms, $X^2$ is a carbon atom or a nitrogen atom, n is 0 when $X^2$ is a nitrogen atom, and is 1 when $X^2$ is a carbon atom, $R^5$ is an acyl group, a dialkylcarbamoyl group, an alkyl carbonate group, an aryl carbonate group, an aralkyl carbonate group, a triflate group, an alkylsulfonyl group, an arylsulfonyl group, an aralkylsulfonyl group, a dialkylsulfamoyl group, or a diarylsulfamoyl group, $R^{11}$ is a hydrogen atom, a hydrocarbon group having 1 to 20 carbon atoms, a group derived therefrom, or an alkoxy group having 1 to 10 carbon atoms, $R^{12}$ is a hydrogen atom, a hydrocarbon group having 1 to 20 carbon atoms, a group derived therefrom, or an alkoxy group having 1 to 10 carbon atoms, $R^{13}$ is a hydrogen atom, a hydrocarbon group having 1 to 20 carbon atoms, a group derived therefrom, or an alkoxy group having 1 to 10 carbon atoms, $R^{14}$ is a hydrogen atom, a hydrocarbon group having 1 to 20 carbon atoms, a group derived therefrom, or an alkoxy group having 1 to 10 carbon atoms, and $R^{15}$ is a hydrogen atom, a hydrocarbon group having 1 to 20 carbon atoms, a group derived therefrom, or an alkoxy group having 1 to 10 carbon atoms, provided that $R^{11}$ and $R^{12}$ optionally bond to each other to form a divalent organic group having 4 to 6 carbon atoms, $R^{12}$ and $R^{13}$ optionally bond to each other to form a divalent organic group having 4 to 6 carbon atoms, $R^{13}$ and $R^{14}$ optionally bond to each other to form a divalent organic group having 4 to 6 carbon atoms, and $R^{14}$ and $R^{15}$ optionally bond to each other to form a divalent organic group having 4 to 6 carbon atoms.)

The meanings of the terms used herein either alone or in combination are described below. The description of each substituent is commonly applied unless otherwise specified. A combination of substituents and the number of substituents is allowed only when a chemically stable compound is produced by such a combination. When a hydrogen atom bonded to a carbon atom is substituted with another atom or a functional group (i.e., substituent), and the substituent is substituted with two or more groups, these groups may be bonded to an identical carbon atom or different carbon atoms as long as a stable structure is obtained.

The term "hydrocarbon group having 1 to 20 carbon atoms" used herein refers to a saturated linear or branched aliphatic hydrocarbon group or alicyclic hydrocarbon group having 1 to 20 carbon atoms. Examples of the hydrocarbon group include a methyl group, an ethyl group, an n-propyl group, an isopropyl group, an n-butyl group, an isobutyl group, a tert-butyl group, an n-pentyl group, an isopentyl group, a neopentyl group, a 1-methylpropyl group, an n-hexyl group, an isohexyl group, a 1,1-dimethylbutyl group, a 2,2-dimethylbutyl group, a 3,3-dimethylbutyl group, an n-heptyl group, an n-octyl group, an n-nonyl group, an n-decyl group, a cyclopropyl group, a cyclobutyl group, a cyclpentyl group, a cyclohexyl group, and the like.

The group derived from the hydrocarbon group having 1 to 20 carbon atoms refers to a group obtained by substituting an arbitrary hydrogen atom bonded to an arbitrary carbon atom included in the hydrocarbon group having 1 to 20 carbon atoms with other atom (e.g., fluorine atom) or a functional group (e.g., ester group, keto group, or cyano group). The number of functional groups (substituents) is not particularly limited.

The term "ester group" used herein refers to a group represented by —COOR (wherein R is a hydrocarbon group having 1 to 20 carbon atoms).

The term "alkoxy group having 1 to 10 carbon atoms" used herein refers to a group that is consisting of an oxy group and a hydrocarbon group having 1 to 9 carbon atoms. Examples of the alkoxy group include a methoxy group, an ethoxy group, an n-propyloxy group, an isopropyloxy group, an n-butyloxy group, an isobutyloxy group, a tert-butyloxy group, a cyclopropoxy group, a cyclobutyloxy group, a cyclopentyloxy group, a cyclohexyloxy group, and the like.

The term "acyl group" used herein refers to a group (R—CO—) obtained by removing —OH from a carboxylic acid (RCOOH). Examples of the acyl group include an acetyl group, a propionyl group, an isopropionyl group, a butanoyl group (butyryl group), an isobutanoyl group, a tert-butanoyl group, a pentanoyl group, an isopentanoyl group, a pivaloyl group, and the like.

The term "dialkylcarbamoyl group" used herein refers to a group obtained by substituting the two hydrogen atoms included in a carbamoyl group (—CONH$_2$) with an identical hydrocarbon group or different hydrocarbon groups. Examples of the dialkylcarbamoyl group include a dimethylcarbamoyl group, a diethylcarbamoyl group, a dipropylcarbamoyl group, a diisopropylcarbamoyl group, a dibutylcarbamoyl group, a diisobutylcarbamoyl group, a di-tert-butylcarbamoyl group, and the like.

The term "alkyl carbonate group" used herein refers to a group represented by RO—CO—O— (wherein R is an alkyl group). Examples of the alkyl carbonate group include a methoxycarbonyloxy group, an ethoxycarbonyloxy group, an n-propoxycarbonyloxy group, an isopropoxycarbonyloxy group, an n-buthoxycarbonyloxy group, a 1-methylpropoxycarbonyloxy group, a 2-methylpropoxycarbonyloxy group, a tert-butoxycarbonyloxy group, and the like.

Examples of the aryl carbonate group include a phenoxycarbonyloxy group, a naphthoxycarbonyloxy group, and the like.

Examples of the aralkyl carbonate group include a benzyloxycarbonyloxy group and the like.

Examples of the alkylsulfonyl group include an alkanesulfonyl group such as a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, and an n-decanesulfonyl group; a cycloalkanesulfonyl group such as a cyclopentanesulfonyl group, and a cyclohexanesulfonyl group; and the like.

Examples of the arylsulfonyl group include a benzenesulfonyl group; an alkylbenzenesulfonyl group such as a tosyl group, a 2,4,6-trimethylbenzenesulfonyl group, a 2,4,6-triethylbenzenesulfonyl group, a 2,4,6-tripropylbenzenesulfonyl group, a 2,4,6-triisopropylbenzenesulfonyl group, and a 2,4,6-tri-tert-butylbenzenesulfonyl group; a naphthalenesulfonyl group; an alkylnaphthalenesulfonyl group; and the like.

Examples of the aralkylsulfonyl group include a benzylsulfonyl group, a 2-phenylethylsulfonyl group, a 4-phenylbutylsulfonyl group, a 2-methylbenzylsulfonyl group, and the like.

Examples of the dialkylsulfamoyl group include an N,N-dimethylsulfamoyl group, an N,N-diethylsulfamoyl group, and the like.

Examples of the diarylsulfamoyl group include a diphenylsulfamoyl group and the like.

A case where adjacent substituents (e.g., $R^1$ and $R^2$ in the general formula (2), or $R^{11}$ and $R^{12}$ in the general formula (3)) bond to each other to form a divalent organic group having 4 to 6 carbon atoms is described below using the compound (heteroaromatic compound) represented by the general formula (2) as an example.

The term "divalent organic group" used herein in connection with the compound (heteroaromatic compound) represented by the general formula (2) refers to (i) a hydrocarbon group or a group derived therefrom in which carbon atoms bond to each other to form a chain-like structure, and which may include a carbon-carbon double bond, wherein, when a hydrogen atom is bonded to an arbitrary carbon atom that forms the chain-like structure, the hydrogen atom is optionally substituted with another atom (e.g., fluorine atom), a functional group (e.g., ester group, keto group, or cyano group), or a monovalent hydrocarbon group, the hydrocarbon group or a group derived therefrom forming a ring together with the carbon atom bonded to the nitrogen atom, and the carbon atom bonded to X', or (ii) an organic group in which a chain-like structure is formed in a state in which a nitrogen atom, an oxygen atom, or a sulfur atom is present between two carbon atoms, and which may include a carbon-carbon double bond, a carbon-nitrogen double bond, or the like, wherein, when a hydrogen atom is bonded to an arbitrary carbon atom that forms the chain-like structure, the hydrogen atom is optionally substituted with another atom (e.g., fluorine atom), a functional group (e.g., ester group, keto group, or cyano group), or a monovalent hydrocarbon group, the organic group forming a ring together with the carbon atom bonded to the nitrogen atom, and the carbon atom bonded to $X^1$.

The heteroaromatic compound represented by the general formula (2) is preferably an oxazole derivative, a benzoxazole derivative, or a benzothiazole derivative, and particularly preferably an oxazole derivative, from the viewpoint of the yield of the resulting product.

When the heteroaromatic compound is an oxazole derivative, it is preferable that one of $R^1$ and $R^2$ be a hydrocarbon group having 1 to 20 carbon atoms or a group derived therefrom from the viewpoint of the yield of the resulting product.

The phenol derivative represented by the general formula (3) (note: a compound represented by the general formula (3) wherein $X^2$ is a nitrogen atom is also referred herein as "phenol derivative") is a compound obtained by substituting a hydroxyl group included in a compound having a phenol skeleton, a compound having a naphthol skeleton, a compound having a hydroxypyridine skeleton, a compound having a quinolinol skeleton, or the like with —$OR^5$ (wherein $R^5$ is an acyl group, a dialkylcarbamoyl group, an alkyl carbonate group, an aryl carbonate group, an aralkyl carbonate group, a triflate group, an alkylsulfonyl group, an arylsulfonyl group, an aralkylsulfonyl group, a dialkylsulfamoyl group, or a diarylsulfamoyl group). $R^5$ is preferably an acyl group, a dialkylcarbamoyl group, an alkyl carbonate group, a triflate group, an alkylsulfonyl group, an arylsulfonyl group, or a dialkylsulfamoyl group from the viewpoint of the yield of the resulting product in the present invention. When $R^5$ is an acyl group, a pivaloyl group is preferable. When $R^5$ is a dialkylcarbamoyl group, an N,N-dimethylcarbamoyl group is preferable. When $R^5$ is an alkyl carbonate group, a tert-butoxycarbonyloxy group is preferable. When $R^5$ is an alkylsulfonyl group, a methanesulfonyl group is preferable. When $R^5$ is an arylsulfonyl group, a tosyl group is preferable. When $R^5$ is a dialkylsulfamoyl group, an N,N-dimethylsulfamoyl group is preferable.

Specific examples of the phenol derivative include compounds respectively represented by the following general formulae (3-1) to (3-16). The phenol derivative is preferably a compound among the compounds respectively represented by the general formulae (3-1) to (3-8) and (3-13) to (3-16) since the target phenyl-substituted heterocyclic derivative can be obtained in high yield.

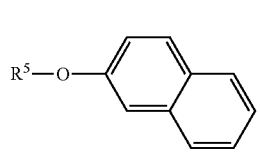
(3-1)

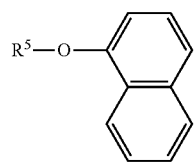
(3-2)

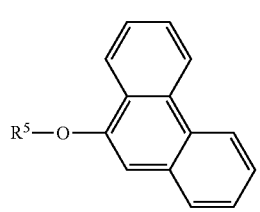
(3-3)

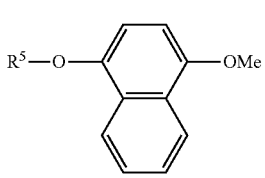
(3-4)

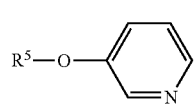
(3-5)

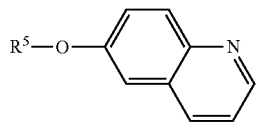
(3-6)

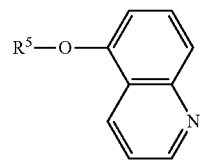
(3-7)

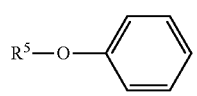
(3-8)

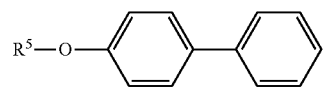
(3-9)

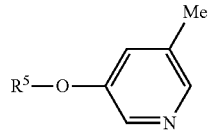
(3-10)

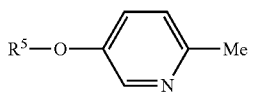
(3-11)

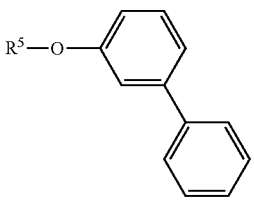
(3-12)

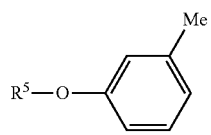
(3-13)

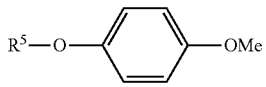
(3-14)

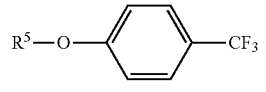
(3-15)

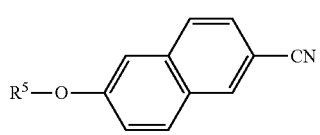
(3-16)

(In the formulae, $R^5$ is an acyl group, a dialkylcarbamoyl group, an alkyl carbonate group, an aryl carbonate group, an aralkyl carbonate group, a triflate group, an alkylsulfonyl group, an arylsulfonyl group, an aralkylsulfonyl group, a dialkylsulfamoyl group, or a diarylsulfamoyl group.)

The phenol derivative may be a compound in which a cyano group, a fluorine atom, or the like is bonded to an arbitrary ring-forming carbon atom included in the compounds respectively represented by the general formulae (3-1) to (3-16).

The heteroaromatic compound and the phenol derivative are used in the ratio described below from the viewpoint of ensuring that the reaction proceeds smoothly.

A usage amount of the phenol derivative is preferably in a range from 1 to 2 mol, and more preferably from 1 to 1.5 mol based on 1 mol of the heteroaromatic compound.

The nickel compound used in the reaction step is not particularly limited. A nickel compound may be used that is conventionally known as a catalyst used for organic synthesis. An Ni(0) salt or an Ni(II) salt are preferable as the nickel compound. These compounds may be used singly or in combination of two or more types thereof.

Examples of the Ni(0) salt include bis(1,5-cyclooctadiene)nickel(0), bis(triphenylphosphine)nickeldicarbonyl, nickelcarbonyl, and the like.

Examples of the Ni(II) salt include nickel acetate (II), nickel trifluoroacetate (II), nickel nitrate (II), nickel chloride (II), nickel bromide (II), nickel acetylacetonate (II), nickel perchlorate (II), nickel citrate (II), nickel oxalate (II), nickel cyclohexanebutyrate (II), nickel benzoate (II), nickel stearate (II), nickel stearate (II), nickel sulfamate (II), nickel carbonate (II), nickel thiocyanate (II), nickel trifluoromethanesulfonate (II), bis(1,5-cyclooctadiene)nickel (II), bis(4-diethylaminodithiobenzyl)nickel (II), nickel cyanide (II), nickel fluoride (II), nickel boride (II), nickel borate (II), nickel hypophosphate (II), ammonium nickel sulfate (II), nickel hydroxide (II), cyclopentadienylnickel (II), hydrates thereof, and the like.

In the present invention, the nickel compound is more preferably an Ni(0) salt and bis(1,5-cyclooctadiene)nickel (0) is particularly preferred from the viewpoint of ensuring that the reaction proceeds smoothly.

An Ni(0) salt or an Ni(II) salt to which a ligand is coordinated in advance may also be used.

A usage amount of the nickel compound is preferably in a range from 0.05 to 0.1 mol, more preferably from 0.08 to 0.1 mol, and further preferably from 0.09 to 0.1 mol based on 1 mol of the heteroaromatic compound from the viewpoint of ensuring that the reaction proceeds smoothly.

1,2-Bis(dicyclohexylphosphino)ethane represented by the following formula is also used in the reaction step. 1,2-Bis(dicyclohexylphosphino)ethane is a ligand that can be coordinated to the nickel atom included in the nickel compound. The reaction between the compound represented by the general formula (2) and the compound represented by the general formula (3) proceeds smoothly in the presence of 1,2-bis(dicyclohexylphosphino)ethane and the nickel compound.

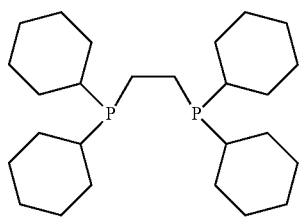

A usage amount of the 1,2-bis(dicyclohexylphosphino)ethane is preferably in a range from 0.1 to 0.2 mol, more preferably from 0.15 to 0.2 mol, and further preferably from 0.18 to 0.2 mol based on 1 mol of the heteroaromatic compound from the viewpoint of ensuring that the reaction proceeds smoothly.

The molar ratio of the Ni atoms included in the nickel compound to 1,2-bis(dicyclohexylphosphino)ethane is preferably 1:1.2 to 1:3, more preferably 1:1.5 to 1:2.5, and particularly 1:2 from the viewpoint of ensuring that the reaction proceeds smoothly.

A base is also used in the reaction step. The base is not particularly limited. A compound may be used that is conventionally known as a base used for organic synthesis. Preferable examples of the base include lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate, potassium acetate, metal salts (lithium salt, sodium salt, or potassium salt) of an alkoxide having 1 to 6 carbon atoms, metal salts (lithium salt, sodium salt, or potassium salt) of an alkyl anion having 1 to 6 carbon atoms, diisopropylethylamine, tributylamine, N-methylmorpholine, diazabicycloundecene, diazabicyclooctane, imidazole, and the like. These compounds may be used singly or in combination of two or more types thereof.

In the present invention, cesium carbonate and tripotassium phosphate are particularly as the base from the viewpoint of ensuring that the reaction proceeds smoothly.

Examples of the alkoxide in case of using the metal salt of the alkoxide having 1 to 6 carbon atoms include a methoxide, an ethoxide, an n-propoxide, an isopropoxide, an n-butoxide, an isobutoxide, a tert-butoxide, an n-pentoxide, an isopentoxide, a neopentoxide, a 1-methylpropoxide, an n-hexoxide, an isohexoxide, a 1,1-dimethylbutoxide, a 2,2-dimethylbutoxide, a 3,3-dimethylbutoxide, and the like.

Examples of the alkyl anion in case of using the metal salt of the alkyl anion having 1 to 6 carbon atoms include a methyl anion, an ethyl anion, an n-propyl anion, an isopropyl anion, an n-butyl anion, an isobutyl anion, a tert-butyl anion, an n-pentyl anion, an isopentyl anion, a neopentyl anion, a 1-methylpropyl anion, an n-hexyl anion, an isohexyl anion, a 1,1-dimethylbutyl anion, a 2,2-dimethylbutyl anion, a 3,3-dimethylbutyl anion, and the like.

A usage amount of the base is preferably in a range from 1 to 2 mol, and more preferably from 1.5 to 2 mol based on 1 mol of the heteroaromatic compound from the viewpoint of ensuring that the reaction proceeds smoothly.

A solvent is normally used in the reaction step. Preferable examples of the solvent include an aliphatic hydrocarbon such as a hexane, a cyclohexane, and a heptane; an aliphatic halogenated hydrocarbon such as a dichloromethane, a chloroform, a carbon tetrachloride, and a dichloroethane; an aromatic hydrocarbon such as a benzene, a toluene, a xylene, and a chlorobenzene; an ether such as a diethyl ether, a dibutyl ether, a dimethoxyethane (DME), a cyclopentyl methyl ether (CPME), a tert-butyl methyl ether, a tetrahydrofuran, and a dioxane; an ester such as ethyl acetate and ethyl propionate; an acid amide such as dimethylformamide (DMF), dimethylacetamide (DMA), and N-methylpyrrolidone (NMP); a nitrile such as acetonitrile and propionitrile; a dimethyl sulfoxide (DMSO), and the like. These compounds may be used singly or in combination of two or more types thereof.

In the present invention, dioxane and DMF are particularly as the solvent from the viewpoint of ensuring that the reaction proceeds smoothly.

The reaction temperature employed in the reaction step is normally in a range from 80° C. to 140° C., preferably from 80° C. to 120° C., and particularly from 100° C. to 120° C. It is desirable to effect the reaction under normal pressure. The reaction may be effected under increased pressure or reduced pressure.

The reaction atmosphere is not particularly limited. The reaction atmosphere is preferably an inert gas atmosphere (e.g., argon gas atmosphere or nitrogen gas atmosphere).

When the heteroaromatic compound is reacted with the phenol derivative (i.e., biaryl coupling reaction) (see the above reaction scheme), the hydrogen atom bonded to the carbon atom indicated by * in the general formula (2) (heteroaromatic compound), and $R^5$—O— bonded to the carbon atom indicated by * in the general formula (3) (phenol derivative) are eliminated, and the carbon atom indicated by * in the general formula (2) and the carbon atom indicated by * in the general formula (3) are bonded to each other. The compound represented by the general formula (1) can be produced by allowing the nickel compound, 1,2-bis(dicyclohexylphosphino)ethane, and the base to be present in combination in the reaction system.

The method may optionally include a purification step after the reaction step. Specifically, the product may be subjected to a normal post-process such as a solvent removal process, a washing process, and a chromatographic process.

The yield of the compound represented by the general formula (1) is preferably 55% or higher, more preferably 70% or higher, and further preferably 80% or higher in the present production method. The term "yield" used herein refers to a value calculated based on the molar quantity of the heteroaromatic compound used as the reaction raw material.

EXAMPLES

Hereinafter, the present invention is specifically described using Examples. The present invention is not limited to these Examples.

Example 1

A glass vessel (internal volume: 20 mL) was charged with magnetic stir bars and 195.5 mg (0.60 mmol) of cesium carbonate, and dried under reduced pressure using a heat gun. The glass vessel was cooled to room temperature, and filled with argon gas.

In a glovebox filled with argon gas, 137.0 mg (0.60 mmol) of naphthalen-2-yl pivalate was added to the glass vessel. Next, 11.2 mg (0.04 mmol) of bis(1,5-cyclooctadiene)nickel (hereinafter referred to as "Ni(cod)$_2$") and 33.8 mg (0.08 mmol) of 1,2-bis(dicyclohexylphosphino)ethane were added to the glass vessel.

After that, the glass vessel was removed from the glovebox, and 47.6 mg (0.40 mmol) of benzoxazole and 1.6 mL of 1,4-dioxane were added to the glass vessel under an argon gas stream.

Subsequently, the glass vessel charged with the raw materials was sealed, and heated at 120° C. with stirring to react the raw materials. After 12 hours, the reaction system was cooled to room temperature, and the reaction mixture was filtered through a short pad of silica gel. A precipitate was washed with ethyl acetate, and the filtrate was concentrated. The concentrate was subjected to TLC (eluant: hexane/ethyl acetate=10/1) using Silica Gel 60 (manufactured by Merck) to obtain 2-(naphthalen-2-yl)benzoxazole (Rf=0.48, white solid) (see below). The amount of 2-(naphthalen-2-yl)benzoxazole obtained was 93.2 mg, and the yield was 95%.

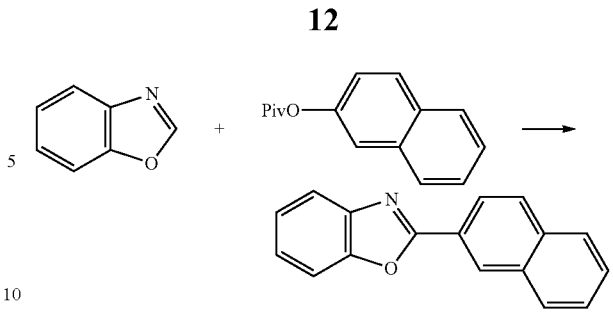

2-(Naphthalen-2-yl)benzoxazole obtained in Example 1 was subjected to NMR analysis ($^1$H-NMR and $^{13}$C-NMR) and mass spectrometry using a nuclear magnetic resonance spectrometer ("JNM-ECA-400" manufactured by JEOL Ltd.) and a TLC/MS system equipped with a DART ion source ("JMS-T100TD" manufactured by JEOL Ltd.), respectively. The results are shown below.

$^1$H-NMR (400 MHz, CDCl$_3$): δ 8.79 (s, 1H), 8.33 (dd, 1H, J=8.7, 1.4 Hz), 8.03-7.96 (m, 2H), 7.93-7.87 (m, 1H), 7.82 (dd, 1H, J=6.0, 3.7 Hz), 7.63 (dd, 1H, J=6.4, 2.7 Hz), 7.60-7.52 (m, 2H), 7.41-7.31 (m, 2H)

$^{13}$C-NMR (100 MHz, CDCl$_3$): δ 163.2, 150.9, 142.2, 134.7, 133.0, 128.9, 128.8, 128.1, 127.9, 127.8, 126.9, 125.2, 124.6, 124.4, 124.0, 120.0, 110.6

HRMS (DART) m/z calcd for C$_{17}$H$_{12}$NO [MH]$^+$: 246.0919. found 246.0919

Example 2

2-(Naphthalen-2-yl)benzoxazole was obtained in the same manner as in Example 1, except using tripotassium phosphate instead of cesium carbonate. The yield thereof was 79%.

Example 3

2-(Naphthalen-2-yl)benzoxazole was obtained in the same manner as in Example 1, except using lithium tert-butoxide instead of cesium carbonate. The yield thereof was 56%.

Example 4

2-(Naphthalen-2-yl)benzoxazole was obtained in the same manner as in Example 1, except using toluene instead of 1,4-dioxane. The yield thereof was 92%.

Example 5

2-(Naphthalen-2-yl)benzoxazole was obtained in the same manner as in Example 1, except using dimethylformamide instead of 1,4-dioxane. The yield thereof was 92%.

Example 6

2-(Naphthalen-2-yl)benzoxazole was obtained in the same manner as in Example 1, except using potassium carbonate instead of cesium carbonate. The yield thereof was 9%.

Comparative Example 1

An operation was performed in the same manner as in Example 1, except using tri(cyclohexyl)phosphine (see below) instead of 1,2-bis(dicyclohexylphosphino)ethane. However, 2-(naphthalen-2-yl)benzoxazole could not be obtained.

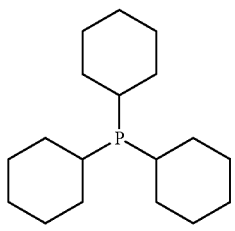 [SMILES: C1CCC(P(C2CCCCC2)C2CCCCC2)CC1]

Comparative Example 2

An operation was performed in the same manner as in Example 1, except using 1,2-bis(diphenylphosphino)ethane (see below) instead of 1,2-bis(dicyclohexylphosphino)ethane. However, 2-(naphthalen-2-yl)benzoxazole could not be obtained.

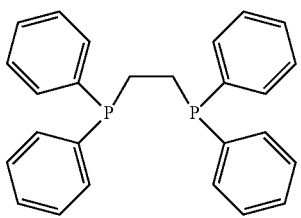 [SMILES: c1ccc(P(CCP(c2ccccc2)c2ccccc2)c2ccccc2)cc1]

Comparative Example 3

2-(Naphthalen-2-yl)benzoxazole was obtained in the same manner as in Example 1, except using 1,2-bis(diethylphosphino)ethane (see below) instead of 1,2-bis(dicyclohexylphosphino)ethane. The yield thereof was 2%.

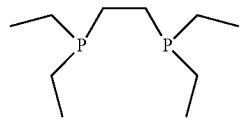

Comparative Example 4

An operation was performed in the same manner as in Example 1, except using 1,2-bis(dimethylphosphino)ethane (see below) instead of 1,2-bis(dicyclohexylphosphino)ethane. However, 2-(naphthalen-2-yl)benzoxazole could not be obtained.

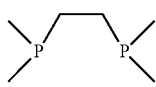

Comparative Example 5

An operation was performed in the same manner as in Example 1, except using 1,3-bis(2,6-diisopropylphenyl)imidazolium chloride (see below) instead of 1,2-bis(dicyclohexylphosphino)ethane. However, 2-(naphthalen-2-yl)benzoxazole could not be obtained.

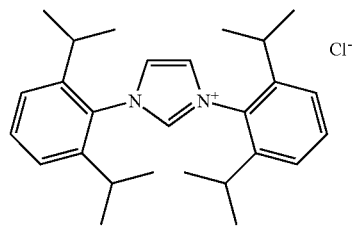 [SMILES: CC(C)c1cccc(C(C)C)c1-n1cc[n+](-c2c(C(C)C)cccc2C(C)C)c1 ; [Cl-]]

Comparative Example 6

An operation was performed in the same manner as in Example 1, except using 2,2'-bipyridyl instead of 1,2-bis(dicyclohexylphosphino)ethane. However, 2-(naphthalen-2-yl)benzoxazole could not be obtained.

Example 7

2-(Naphthalen-2-yl)oxazole (see below) was obtained in the same manner as in Example 1, except using oxazole instead of benzoxazole. The yield thereof was 38%.

The following is an analytical result of 2-(naphthalen-2-yl)oxazole.

$^1$H-NMR (400 MHz, CDCl$_3$): δ 8.55 (s, 1H), 8.14 (dd, 1H, J=9.2, 1.8 Hz), 7.97-7.83 (m, 1H), 7.77 (s, 1H), 7.56-7.51 (m, 2H), 7.29 (s, 1H)

$^{13}$C-NMR (100 MHz, CDCl$_3$): δ 162.2, 138.7, 134.1, 133.0, 128.72, 128.65, 128.6, 127.8, 127.3, 126.7, 126.3, 124.8, 123.3

HRMS (DART) m/z calcd for C$_{13}$H$_{10}$NO [MH]$^+$: 196.0762. found 196.0763

Example 8

Methyl-5-methyl-2-(naphthalen-2-yl)oxazole-4-carboxylate (see below) was obtained in the same manner as in Example 1, except using methyl 5-methyl-1,3-oxazole-4-carboxylate instead of benzoxazole. The yield thereof was 72%.

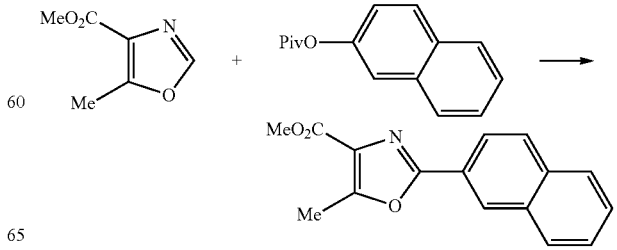

The following is an analytical result of methyl-5-methyl-2-(naphthalen-2-yl)oxazole-4-carboxylate.

¹H-NMR (400 MHz, CDCl₃): δ 8.54 (s, 1H), 8.11 (dd, 1H, J=8.7, 1.8 Hz), 7.93-7.78 (m, 3H), 7.53-7.47 (m, 2H), 3.95 (s, 3H), 2.71 (s, 3H)

¹³C-NMR (100 MHz, CDCl₃): δ 162.7, 159.7, 156.4, 134.1, 132.8, 128.6, 128.53, 128.48, 127.7, 127.3, 126.7, 126.5, 123.7, 123.1, 51.9, 12.1

HRMS (DART) m/z calcd for $C_{16}H_{14}NO_3$ [MH]⁺: 268.0974. found 268.0974

Example 9

Ethyl-2-(naphthalen-2-yl)oxazole-5-carboxylate (see below) was obtained in the same manner as in Example 1, except using ethyl 5-oxazolecarboxylate instead of benzoxazole. The yield thereof was 34%.

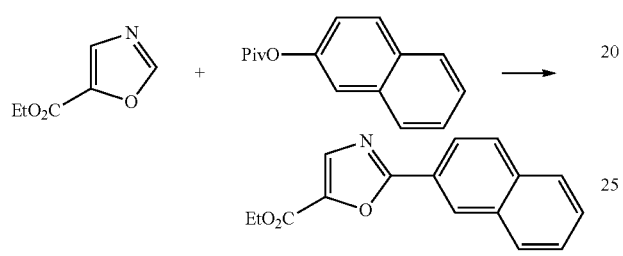

The following is an analytical result of ethyl-2-(naphthalen-2-yl)oxazole-5-carboxylate.

¹H-NMR (400 MHz, CDCl₃): δ 8.67 (s, 1H), 8.18 (dd, 1H, J=8.7, 1.8 Hz), 7.99-7.80 (m, 4H), 7.60-7.49 (m, 2H), 4.44 (q, 2H, J=7.3 Hz), 1.43 (t, 3H, J=7.3 Hz)

¹³C-NMR (100 MHz, CDCl₃): δ 164.3, 157.9, 142.4, 135.4, 134.6, 132.8, 128.9, 128.8, 127.84, 127.76, 126.9, 123.6, 123.4, 61.5, 14.3

HRMS (DART) m/z calcd for $C_{16}H_{14}NO_3$ [MH]⁺: 268.0974. found 268.0973

Example 10

2-(Naphthalen-2-yl)-5-phenyloxazole (see below) was obtained in the same manner as in Example 1, except using 5-phenyloxazole instead of benzoxazole. The yield thereof was 82%.

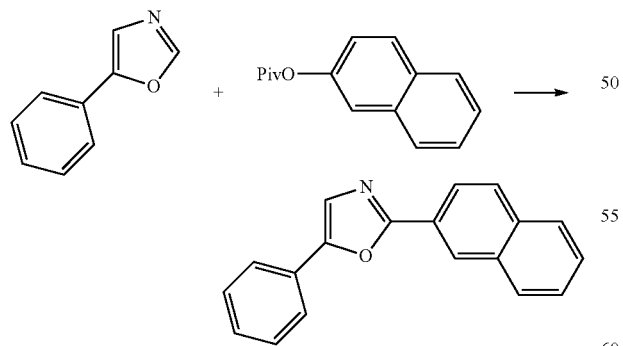

The following is an analytical result of 2-(naphthalen-2-yl)-5-phenyloxazole.

¹H-NMR (400 MHz, CDCl₃): δ 8.55 (s, 1H), 8.16 (dd, 1H, J=8.2, 1.8 Hz), 7.95-7.86 (m, 2H), 7.86-7.77 (m, 1H), 7.72 (d, 2H, J=7.8 Hz), 7.53-7.34 (m, 2H), 7.47-7.38 (m, 3H), 7.32 (t, 1H, J=7.8 Hz)

¹³C-NMR (100 MHz, CDCl₃): δ 162.2, 151.3, 134.1, 133.0, 128.9, 128.62, 128.58, 128.4, 127.9, 127.8, 127.1, 126.7, 126.0, 124.6, 124.2, 123.6, 123.2

HRMS (DART) m/z calcd for $C_{19}H_{14}NO$ [MH]⁺: 272.1075. found 272.1075

Example 11

5-(Benzo[1,3,]dioxol-5-yl)-2-(naphthalen-2-yl)oxazole (see below) was obtained in the same manner as in Example 1, except using 5-(1,3-benzodioxol-5-yl)oxazole instead of benzoxazole. The yield thereof was 72%.

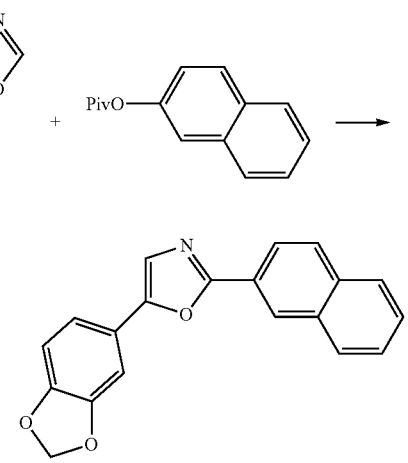

The following is an analytical result of 5-(benzo[1,3,]dioxol-5-yl)-2-(naphthalen-2-yl)oxazole.

¹H-NMR (400 MHz, CDCl₃): δ 8.49 (s, 1H), 8.11 (dd, 1H, J=8.6, 1.8 Hz), 7.93-7.78 (m, 3H), 7.52-7.45 (m, 2H), 7.30 (s, 1H), 7.22 (dd, 1H, J=8.2, 1.8 Hz), 7.14 (s, 1H), 6.84 (d, 1H, J=8.2 Hz), 5.94 (s, 2H)

¹³C-NMR (100 MHz, CDCl₃): δ 160.6, 151.2, 148.1, 147.8, 133.9, 133.0, 128.6, 128.5, 127.8, 127.0, 126.6, 125.8, 124.6, 123.1, 122.4, 122.1, 118.3, 108.7, 104.7, 101.3

HRMS (DART) m/z calcd for $C_{20}H_{14}NO_3$ [MH]⁺: 316.0974. found 316.0973

Example 12

2-(Naphthalen-2-yl)thiazole (see below) was obtained in the same manner as in Example 1, except that thiazole was used instead of benzoxazole, cesium carbonate was used in an amount of 0.80 mmol, and the reaction temperature was changed to 140° C. The yield thereof was 47%.

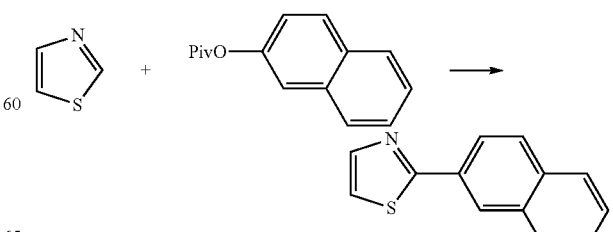

The following is an analytical result of 2-(naphthalen-2-yl)thiazole.

¹H-NMR (400 MHz, CDCl₃): δ 8.43 (d, 1H, J=1.4 Hz), 8.07 (dd, 1H, J=8.7, 1.8 Hz), 7.92-7.86 (m, 3H), 7.83 (dd, 1H, J=6.0, 3.2 Hz), 7.53-7.47 (m, 2H), 7.33 (d, 1H, J=3.2 Hz)

¹³C-NMR (100 MHz, CDCl₃): δ 168.4, 143.8, 134.0, 133.2, 130.9, 128.7, 128.6, 127.8, 126.9, 126.7, 125.9, 124.0, 118.9

HRMS (DART) m/z calcd for $C_{13}H_{10}NS$ [MH]⁺: 212.0534. found 212.0534

Example 13

2-(Naphthalen-2-yl)benzothiazole (see below) was obtained in the same manner as in Example 1, except that benzothiazole was used instead of benzoxazole, cesium carbonate was used in an amount of 0.80 mmol, and the reaction temperature was changed to 140° C. The yield thereof was 65%.

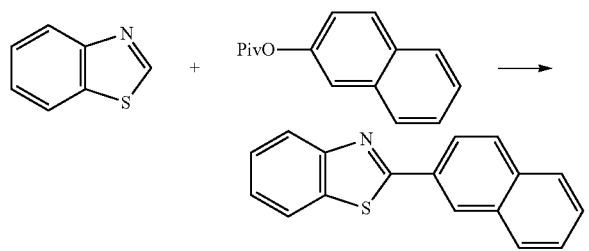

The following is an analytical result of 2-(naphthalen-2-yl)benzothiazole.

¹H-NMR (400 MHz, CDCl₃): δ 8.57 (d, 1H, J=1.2 Hz), 8.21 (dd, 1H, J=8.8, 2.0 Hz), 8.12 (dt, 1H, J=8.4, 0.4 Hz), 8.01-7.92 (m, 3H), 7.91-7.84 (m, 1H), 7.60-7.49 (m, 3H), 7.41 (td, 1H, J=8.0, 1.2 Hz)

¹³C-NMR (100 MHz, CDCl₃): δ 168.0, 154.2, 135.1, 134.5, 133.1, 130.9, 128.7, 127.8, 127.5, 127.4, 126.8, 126.3, 125.1, 124.3, 123.2, 121.6

HRMS (DART) m/z calcd for $C_{17}H_{12}NS$ [MH]⁺: 262.0690. found 262.0690

Example 14

2-(Naphthalen-2-yl)benzoxazole (see below) was obtained in the same manner as in Example 1, except using (naphthalen-2-yl)dimethyl carbamate instead of naphthalen-2-yl pivalate. The yield thereof was 93%.

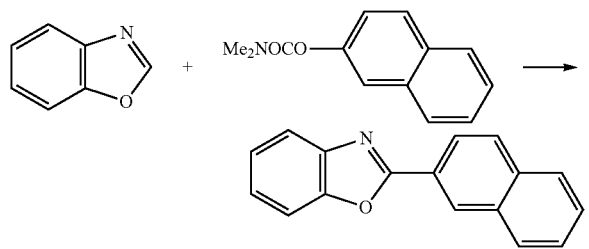

Example 15

Methyl-6-(benzo[d]oxazol-2-yl)-2-naphthoate (see below) was obtained in the same manner as in Example 1, except using methyl-6-(pivaloyloxy)-2-naphthoate instead of naphthalen-2-yl pivalate. The yield thereof was 28%.

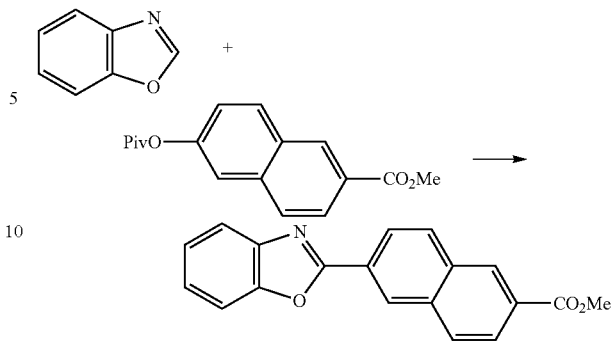

The following is an analytical result of methyl-6-(benzo[d]oxazol-2-yl)-2-naphthoate.

¹H-NMR (400 MHz, CDCl₃): δ 8.76 (s, 1H), 8.62 (s, 1H), 8.35 (d, 1H, J=8.4 Hz), 8.12 (dd, 1H, J=8.0, 1.2 Hz), 8.05 (d, 1H, J=8.8 Hz), 8.00 (d, 1H, J=8.8 Hz), 7.85-7.72 (m, 1H), 7.65-7.54 (m, 1H), 7.43-7.30 (m, 2H), 3.99 (s, 3H)

¹³C-NMR (100 MHz, CDCl₃): δ 166.8, 162.6, 150.9, 142.1, 135.0, 133.7, 130.8, 130.1, 129.1, 129.0, 127.6, 126.5, 126.3, 125.5, 124.8, 124.7, 120.2, 110.7, 52.4

HRMS (DART) m/z calcd for $C_{19}H_{14}NO_3$ [MH]⁺: 304.0974. found 304.0973

Example 16

2-(Naphthalen-1-yl)benzoxazole (see below) was obtained in the same manner as in Example 1, except using naphthalen-1-yl pivalate instead of naphthalen-2-yl pivalate. The yield thereof was 90%.

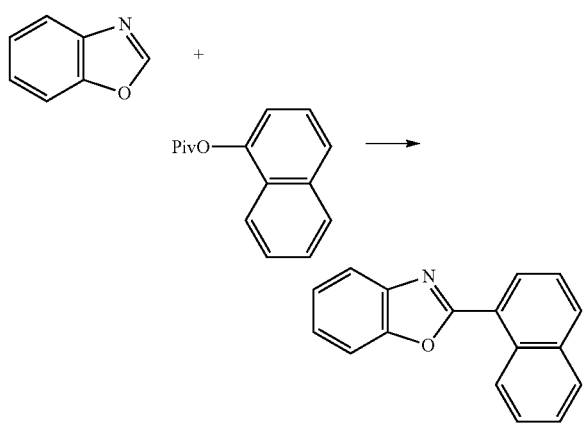

The following is an analytical result of 2-(naphthalen-1-yl)benzoxazole.

¹H-NMR (400 MHz, CDCl₃): δ 9.47 (d, 1H, J=8.4 Hz), 8.38 (d, 1H, J=7.2 Hz), 7.97 (d, 1H, J=8.0 Hz), 7.91-7.82 (m, 2H), 7.68 (t, 1H, J=8.0 Hz), 7.62-7.57 (m, 1H), 7.54 (t, 2H, J=8.4 Hz), 7.40-7.31 (m, 2H)

¹³C-NMR (100 MHz, CDCl₃): δ 162.7, 150.1, 142.3, 133.9, 132.2, 130.6, 129.3, 128.6, 127.8, 126.4, 126.2, 125.2, 124.8, 124.4, 123.5, 120.1, 110.4

HRMS (DART) m/z calcd for $C_{17}H_{12}NO$ [MH]⁺: 246.0919. found 246.0918

Example 17

2-(Phenanthren-9-yl)benzoxazole (see below) was obtained in the same manner as in Example 1, except using 9-phenanthryl pivalate ((phenanthren-9-yl) pivalate) instead of naphthalen-2-yl pivalate. The yield thereof was 55%.

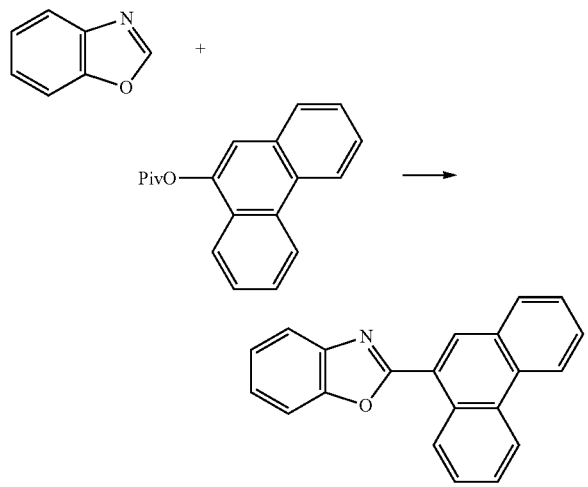

The following is an analytical result of 2-(phenanthren-9-yl)benzoxazole.

$^1$H-NMR (400 MHz, CDCl$_3$): δ 9.54 (dd, 1H, J=8.2, 2.0 Hz), 8.80 (dd, 1H, J=2.1, 7.5 Hz) 8.78-8.72 (m, 2H), 8.04, (d, 1H, J=8.0 Hz), 7.95-7.88 (m, 1H), 7.84-7.74 (m, 3H), 7.73-7.63 (m, 2H), 7.46-7.39 (m, 2H)

$^{13}$C-NMR (100 MHz, CDCl$_3$): δ 162.6, 150.1, 142.2, 131.7, 131.5, 130.7, 130.4, 129.7, 128.61, 128.58, 127.6, 127.0, 125.3, 124.5, 122.9, 122.6, 122.4, 120.3, 110.5

HRMS (DART) m/z calcd for C$_{21}$H$_{14}$NO [MH]$^+$: 296.1075. found 296.1075

Example 18

2-(4-Methoxynaphthalen-1-yl)benzo[d]oxazole (see below) was obtained in the same manner as in Example 1, except using (4-methoxynaphthalen-1-yl) pivalate instead of naphthalen-2-yl pivalate. The yield thereof was 55%.

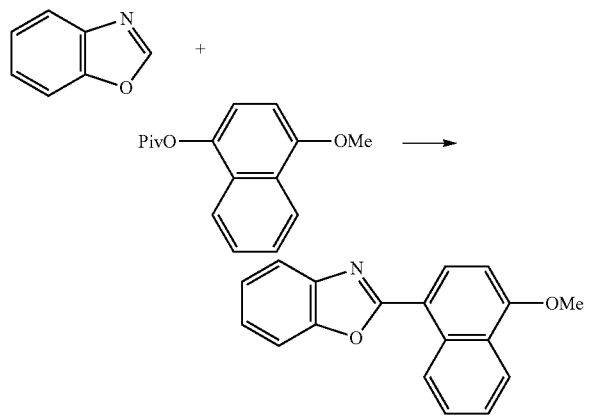

The following is an analytical result of 2-(4-methoxynaphthalen-1-yl)benzo[d]oxazole.

$^1$H-NMR (400 MHz, CDCl$_3$): δ 9.45 (d, 1H, J=8.8 Hz), 8.42-8.36 (m, 2H), 7.84 (td, 1H, J=4.4, 1.8 Hz), 7.72 (td, 1H, J=7.7, 1.8 Hz), 7.63-7.54 (m, 2H), 7.39-7.33 (m, 2H), 6.93 (d, 1H, J=8.4 Hz), 4.08 (s, 3H)

$^{13}$C-NMR (100 MHz, CDCl$_3$): δ 163.1, 158.4, 150.0, 142.5, 131.8, 130.5, 128.4, 126.1, 125.8, 124.7, 124.3, 122.4, 119.9, 116.0, 110.2, 103.2, 55.8

HRMS (DART) m/z calcd for C$_{18}$H$_{14}$NO$_2$ [MH]$^+$: 276.1025. found 276.1024

Example 19

2-(Pyridin-3-yl)benzoxazole (see below) was obtained in the same manner as in Example 1, except using (pyridin-3-yl) pivalate instead of naphthalen-2-yl pivalate. The yield thereof was 81%.

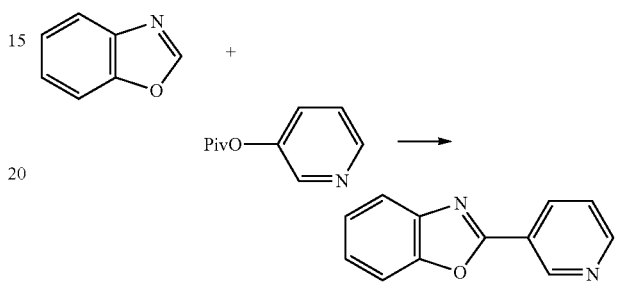

The following is an analytical result of 2-(pyridin-3-yl)benzoxazole.

$^1$H-NMR (400 MHz, CDCl$_3$): δ 9.48 (s, 1H), 8.76 (dd, 1H, J=3.4, 1.8 Hz), 8.51 (d, 1H, J=8.2 Hz), 7.84-7.76 (m, 1H), 7.65-7.58 (m, 1H), 7.50-7.43 (m, 1H), 7.43-7.35 (m, 2H)

$^{13}$C-NMR (100 MHz, CDCl$_3$): δ 160.5, 151.9, 150.6, 148.6, 141.6, 134.5, 125.6, 124.8, 123.5, 123.4, 120.1, 110.6

HRMS (DART) m/z calcd for C$_{12}$H$_9$N$_2$O [MH]$^+$: 197.0715. found 197.0715

Example 20

2-(Quinolin-6-yl)benzoxazole (see below) was obtained in the same manner as in Example 1, except using (quinolin-6-yl) pivalate instead of naphthalen-2-yl pivalate. The yield thereof was 99%.

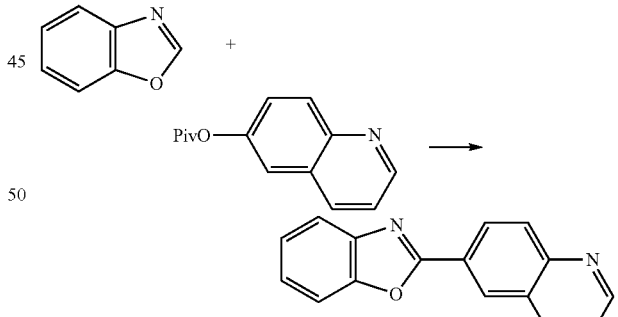

The following is an analytical result of 2-(quinolin-6-yl)benzoxazole.

$^1$H-NMR (400 MHz, CDCl$_3$): δ 9.04-8.97 (m, 1H), 8.76 (s, 1H), 8.56 (dt, 1H, J=7.3, 1.8 Hz), 8.29 (d, 1H, J=8.2 Hz), 8.24 (d, 1H, J=8.7 Hz), 7.86-7.79 (m, 1H), 7.68-7.59 (m, 1H), 7.53-7.46 (m, 1H), 7.44-7.36 (m, 1H)

$^{13}$C-NMR (100 MHz, CDCl$_3$): δ 162.4, 152.0, 150.9, 149.5, 142.1, 136.8, 130.4, 128.0, 127.9, 127.7, 125.5, 125.2, 124.8, 122.1, 120.2, 110.7

HRMS (DART) m/z calcd for C$_{16}$H$_{11}$N$_2$O [MH]$^+$: 247.0871. found 247.0871

Example 21

2-(Quinolin-5-yl)benzoxazole (see below) was obtained in the same manner as in Example 1, except using (quinolin-5-yl) pivalate instead of naphthalen-2-yl pivalate. The yield thereof was 86%.

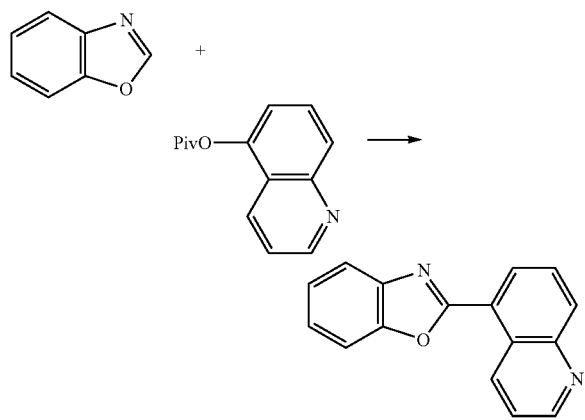

The following is an analytical result of 2-(quinolin-5-yl) benzoxazole.

$^1$H-NMR (400 MHz, CDCl$_3$): δ 9.93 (d, 11-1, J=8.2 Hz), 9.00 (dd, 1H, J=4.1, 1.4 Hz), 8.49 (dd, 1H, J=7.3, 0.9 Hz), 8.29 (d, 1H, J=8.2 Hz), 7.90-7.78 (m, 2H), 7.67-7.56 (m, 2H), 7.45-7.36 (m, 2H)

$^{13}$C-NMR (100 MHz, CDCl$_3$): δ 161.6, 150.8, 150.0, 148.4, 142.1, 135.0, 133.6, 129.3, 128.5, 126.3, 125.6, 124.7, 123.7, 122.5, 120.3, 110.6

HRMS (DART) m/z calcd for C$_{16}$H$_{11}$N$_2$O [MH]$^+$: 247.0871. found 247.0872

Example 22

2-Phenylbenzoxazole (see below) was obtained in the same manner as in Example 1, except using phenyl pivalate instead of naphthalen-2-yl pivalate. The yield thereof was 11%.

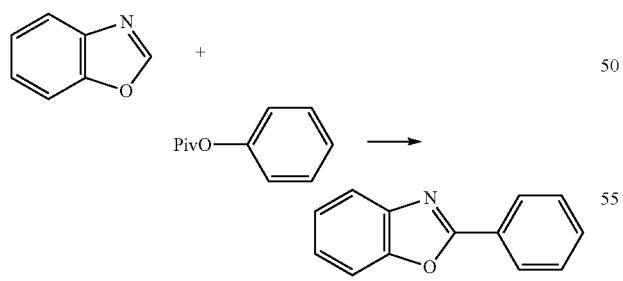

The following is an analytical result of 2-phenylbenzoxazole.

$^1$H-NMR (400 MHz, CDCl$_3$): δ 8.27 (dd, 2H, J=8.9, 1.8 Hz), 7.78 (dd, 1H, J=5.7, 3.7 Hz), 7.59 (dd, 1H, J=6.4, 3.2 Hz), 7.56-7.49 (m, 3H), 7.38-7.34 (m, 2H)

$^{13}$C-NMR (100 MHz, CDCl$_3$): δ 163.0, 150.7, 142.1, 131.4, 128.8, 127.6, 127.1, 125.0, 124.5, 120.0, 110.5

HRMS (DART) m/z calcd for C$_{13}$H$_{10}$NO [MH]$^+$: 196.0762. found 196.0762

Example 23

2-[(1,1'-Biphenyl-4-yl)benzo[d]oxazole] (see below) was obtained in the same manner as in Example 1, except using (1,1'-biphenyl)-4-yl pivalate instead of naphthalen-2-yl pivalate. The yield thereof was 18%.

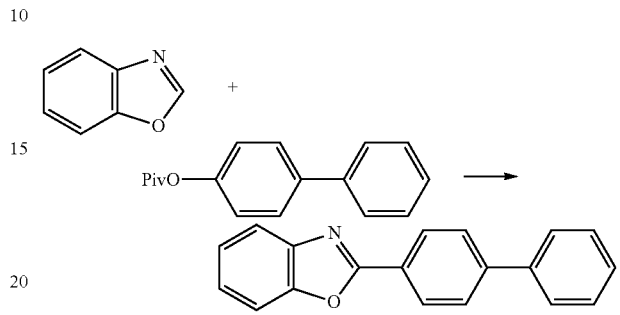

The following is an analytical result of 2-[(1,1'-biphenyl-4-yl)benzo[d]oxazole].

$^1$H-NMR (400 MHz, CDCl$_3$): δ 8.33 (d, 2H, J=8.2 Hz), 7.83-7.72 (m, 3H), 7.67 (d, 2H, J=7.3 Hz), 7.63-7.57 (m, 1H), 7.49 (t, 2H, J=8.2, 7.3 Hz), 7.43-7.31 (m, 3H)

$^{13}$C-NMR (100 MHz, CDCl$_3$): δ 162.9, 150.8, 144.2, 142.2, 140.0, 129.0, 128.1, 127.6, 127.2, 126.0, 125.1, 124.6, 120.0, 110.6

HRMS (DART) m/z calcd for C$_{19}$H$_{14}$NO [MH]$^+$: 272.1075. found 272.1076

Example 24

2-[(1,1'-Biphenyl-3-yl)benzo[d]oxazole] (see below) was obtained in the same manner as in Example 1, except using (1,1'-biphenyl)-3-yl pivalate instead of naphthalen-2-yl pivalate. The yield thereof was 14%.

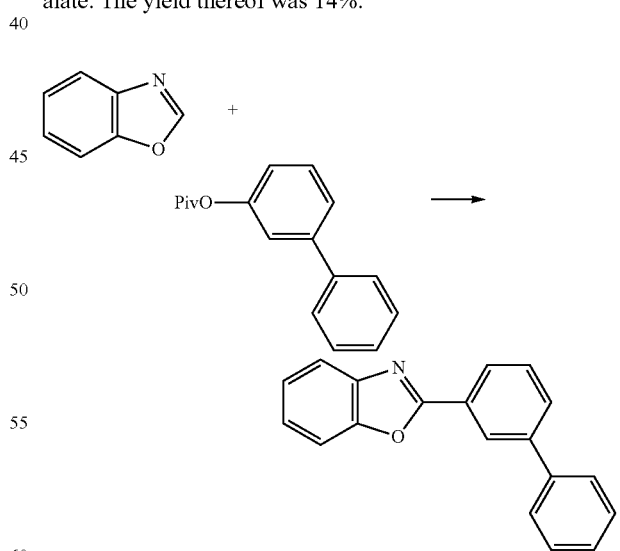

The following is an analytical result of 2-[(1,1'-biphenyl-3-yl)benzo[d]oxazole].

$^1$H-NMR (400 MHz, CDCl$_3$): δ 8.51 (t, 1H, J=1.6 Hz), 8.23 (dt, 1H, J=8.0, 1.6, 1.2 Hz), 7.83-7.78 (m, 1H), 7.76 (dt, 1H, J=8.0, 1.6 Hz), 7.70 (d, 2H, J=7.2 Hz), 7.63-7.57 (m, 2H), 7.51-7.45 (m, 2H), 7.43-7.33 (m, 3H)

$^{13}$C-NMR (100 MHz, CDCl$_3$): δ 163.0, 150.8, 142.1, 142.0, 140.1, 130.2, 129.4, 128.9, 127.8, 127.7, 127.2, 126.4, 126.3, 125.2, 124.6, 120.0, 110.6

HRMS (DART) m/z calcd for C$_{19}$H$_{14}$NO [MH]$^+$: 272.1075. found 272.1076

Example 25

2-(5-Methylpyridin-3-yl)benzo[d]oxazole (see below) was obtained in the same manner as in Example 1, except using 5-methylpyridin-3-yl pivalate instead of naphthalen-2-yl pivalate. The yield thereof was 26%.

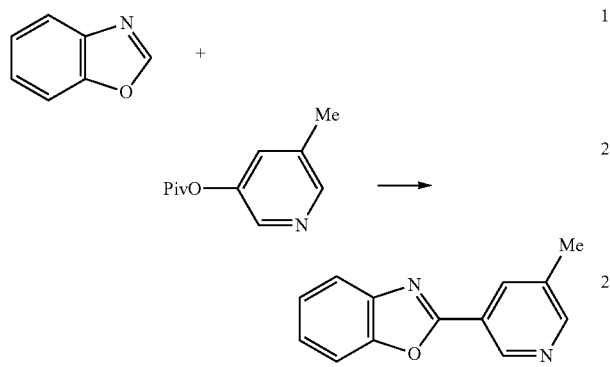

The following is an analytical result of 2-(5-methylpyridin-3-yl)benzo[d]oxazole.

$^1$H-NMR (400 MHz, CDCl$_3$): δ 8.64 (d, 1H, J=5.0 Hz), 8.45 (dd, 1H, J=8.2 Hz), 7.82 (t, 1H, J=6.0, 3.2 Hz), 7.61 (t, 1H, J=5.5, 4.6 Hz), 7.43-7.35 (m, 2H), 7.34-7.28 (m, 1H), 3.07 (s, 3H)

$^{13}$C-NMR (100 MHz, CDCl$_3$): δ 161.6, 158.4, 150.8, 150.5, 141.9, 137.3, 125.5, 124.7, 122.4, 121.1, 120.4, 110.6, 25.3

HRMS (DART) m/z calcd for C$_{19}$H$_{14}$NO [MH]$^+$: 211.0871. found 211.0871

Example 26

2-(6-Methylpyridin-3-yl)benzo[d]oxazole (see below) was obtained in the same manner as in Example 1, except using 6-methylpyridin-3-yl pivalate instead of naphthalen-2-yl pivalate. The yield thereof was 32%.

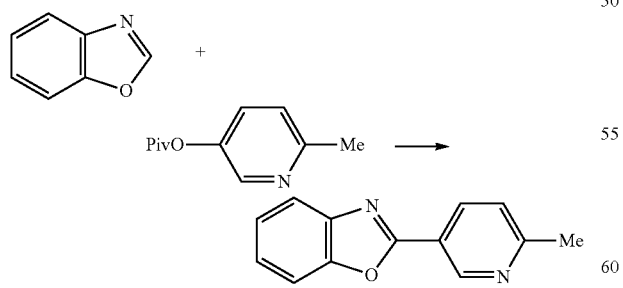

The following is an analytical result of 2-(6-methylpyridin-3-yl)benzo[d]oxazole.

$^1$H-NMR (400 MHz, CDCl$_3$): δ 9.35 (d, 1H, J=1.6 Hz), 8.39 (dd, 1H, J=8.4, 2.4 Hz), 7.81-7.75 (m, 1H), 7.63-7.57 (m, 1H), 7.41-7.35 (m, 2H), 7.32 (d, 1H, J=8.0 Hz), 2.66 (s, 3H)

$^{13}$C-NMR (100 MHz, CDCl$_3$): δ 161.6, 161.1, 150.6, 148.2, 141.8, 135.0, 125.4, 124.8, 123.4, 120.8, 120.1, 110.7, 24.6

HRMS (DART) m/z calcd for C$_{13}$H$_{11}$N$_2$O [MH]$^+$: 211.0871. found 211.0872

Example 27

2-(Naphthalen-2-yl)benzoxazole was obtained in the same manner as in Example 1, except using naphthalen-2-yl-tert-butyl carbonate instead of naphthalen-2-yl pivalate. The yield thereof was 80%.

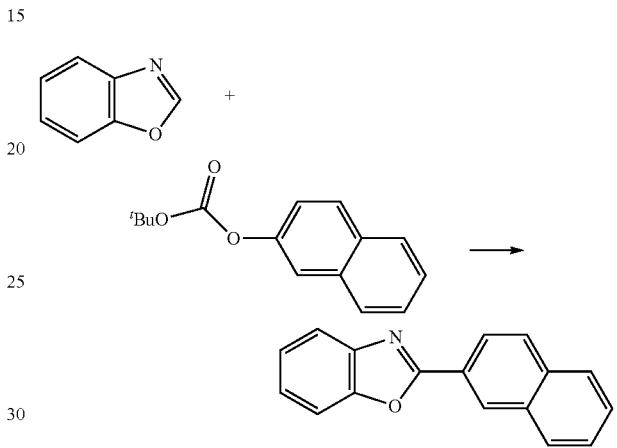

Example 28

2-(Naphthalen-2-yl)benzoxazole was obtained in the same manner as in Example 1, except using naphthalen-2-yl-N,N-dimethyl sulfamate instead of naphthalen-2-yl pivalate. The yield thereof was 82%.

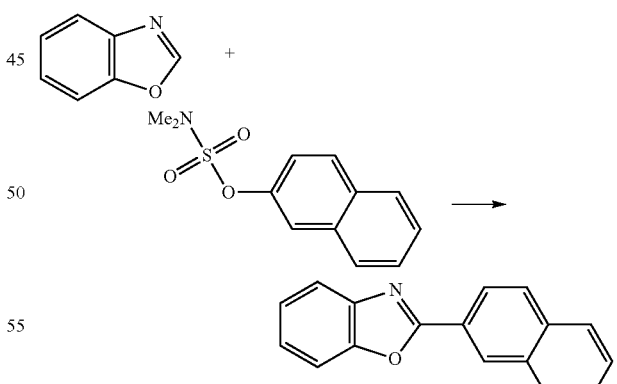

Example 29

2-(Naphthalen-2-yl)benzoxazole was obtained in the same manner as in Example 1, except using naphthalen-2-yl triflate instead of naphthalen-2-yl pivalate. The yield thereof was about 100%.

Example 30

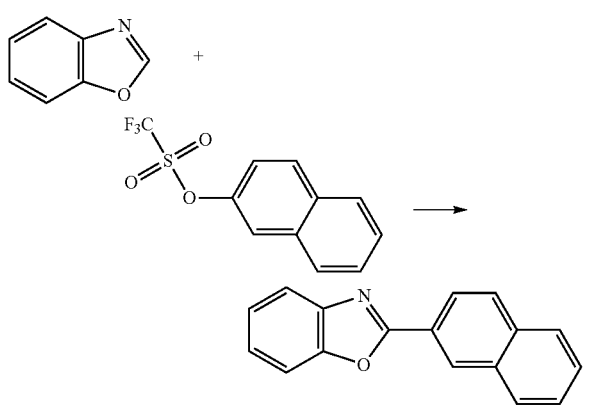

2-(Naphthalen-2-yl)benzoxazole was obtained in the same manner as in Example 1, except using naphthalen-2-yl tosylate instead of naphthalen-2-yl pivalate. The yield thereof was 79%.

Example 31

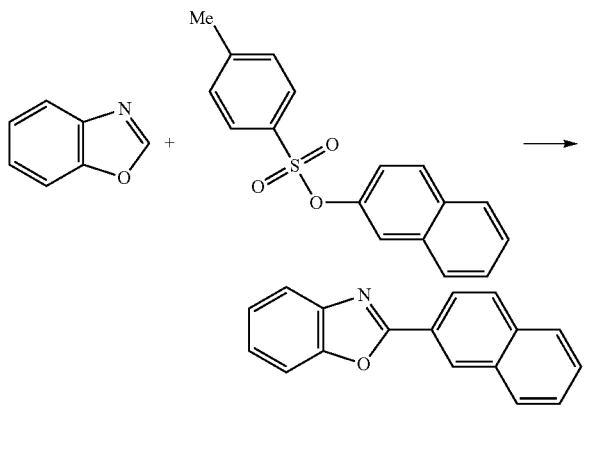

2-(Naphthalen-2-yl)benzoxazole was obtained in the same manner as in Example 1, except using naphthalen-2-yl mesilate instead of naphthalen-2-yl pivalate. The yield thereof was 89%.

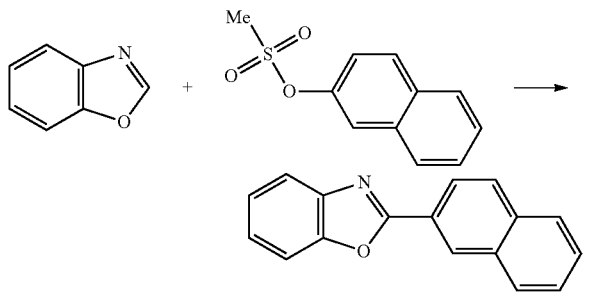

Example 32

2-Phenylbenzoxazole was obtained in the same manner as in Example 1, except using phenyl triflate instead of naphthalen-2-yl pivalate. The yield thereof was 75%.

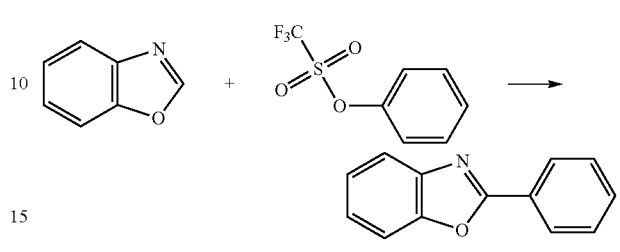

The following is an analytical result of 2-phenylbenzoxazole.

$^1$H NMR (400 MHz, CDCl$_3$): δ 8.30-8.24 (m, 2H), 7.78 (dd, 1H, J=5.6, 3.2 Hz), 7.59 (dd, 1H, J=6.4, 3.2 Hz), 7.56-7.49 (m, 3H) 7.38-7.34 (m, 2H)

$^{13}$C NMR (100 MHz, CDCl$_3$): δ 163.0, 150.7, 142.1, 131.4, 128.8, 127.6, 127.1, 125.0, 124.5, 120.0, 110.5

HRMS (DART) m/z calcd for C$_{13}$H$_{10}$NO [MH]$^+$: 196.0762. found 196.0762

Example 33

2-(3-Methylphenyl)benzoxazole was obtained in the same manner as in Example 1, except using 3-methylphenyl triflate instead of naphthalen-2-yl pivalate. The yield thereof was 85%.

The following is an analytical result of 2-(3-methylphenyl)benzoxazole.

$^1$H NMR (400 MHz, CDCl$_3$): δ 8.07 (s, 1H), 8.02 (d, 1H, J=7.6 Hz), 7.79-7.71 (m, 1H), 7.58-7.49 (m, 1H), 7.41-7.27 (m, 4H), 2.41 (s, 3H)

$^{13}$C NMR (100 MHz, CDCl$_3$): δ 163.1, 150.6, 142.1, 138.6, 132.2, 128.7, 128.1, 126.9, 124.9, 124.6, 124.4, 119.8, 110.4, 21.2

HRMS (DART) m/z calcd for C$_{14}$H$_{12}$NO [MH]$^+$: 210.0919. found 210.0919

Example 34

2-(4-Methoxyphenyl)benzoxazole was obtained in the same manner as in Example 1, except using 4-methoxyphenyl triflate instead of naphthalen-2-yl pivalate. The yield thereof was 55%.

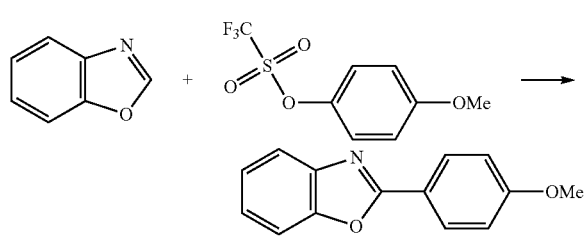

The following is an analytical result of 2-(4-methoxyphenyl)benzoxazole.

$^1$H NMR (400 MHz, CDCl$_3$): δ 8.18 (dd, 2H, J=9.2, 1.4 Hz), 7.72 (dd, 1H, J=6.9, 2.3 Hz), 7.53 (dd, 1H, J=6.0, 2.3 Hz), 7.37-7.27 (m, 2H) 7.00 (dd, 2H, J=8.9, 1.4 Hz) 3.85 (s, 3H)

$^{13}$C NMR (100 MHz, CDCl$_3$): δ 163.1, 162.2, 150.6, 142.2, 129.3, 124.5, 124.3, 119.6, 119.5, 114.3, 110.3, 55.4

HRMS (DART) m/z calcd for C$_{14}$H$_{12}$NO$_2$ [MH]$^+$: 226.0868. found 226.0868

Example 35

2-(4-Trifluoromethylphenyl)benzoxazole was obtained in the same manner as in Example 1, except using 4-trifluoromethylphenyl triflate instead of naphthalen-2-yl pivalate. The yield thereof was 52%.

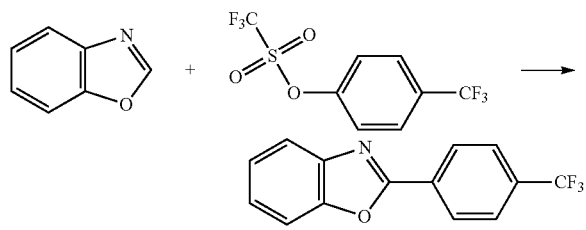

The following is an analytical result of 2-(4-trifluoromethylphenyl)benzoxazole.

$^1$H NMR (400 MHz, CDCl$_3$): δ 8.34 (d, 2H, J=7.8 Hz), 7.82-7.73 (m, 3H), 7.62-7.55 (m, 1H), 7.41-7.34 (m, 2H)

$^{13}$C NMR (100 MHz, CDCl$_3$): δ 161.4, 150.8, 141.9, 132.9 (JC-F=33.5 Hz), 130.4, 127.8, 125.9 (JC-F=3.8 Hz), 125.8, 124.9, 123.7 (JC-F=274.0 Hz), 120.4, 110.8

HRMS (DART) m/z calcd for C$_{14}$H$_9$F$_3$NO [MH]$^+$: 264.0636. found 264.0635

Example 36

2-(6-Cyanonaphthalen-2-yl)benzoxazole was obtained in the same manner as in Example 1, except using 6-cyanonaphthalen-2-yl pivalate instead of naphthalen-2-yl pivalate. The yield thereof was 79%.

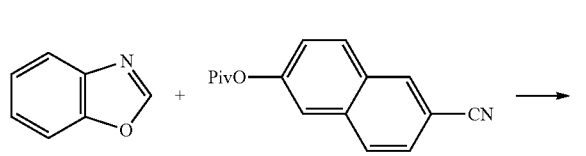

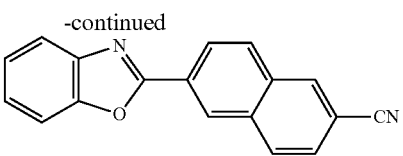

The following is an analytical result of 2-(6-cyanonaphthalen-2-yl)benzoxazole.

$^1$H NMR (400 MHz, CDCl$_3$): δ 8.73 (s, 1H), 8.38 (dd, 1H, J=8.7, 1.4 Hz), 8.22 (s, 1H), 8.00 (t, 2H, J=9.9 Hz), 7.84-7.76 (m, 1H), 7.64 (dd, 1H, J=8.7, 0.9 Hz), 7.63-7.57 (m, 1H), 7.45-7.35 (m, 2H)

$^{13}$C NMR (100 MHz, CDCl$_3$): δ 161.9, 150.8, 142.0, 134.2, 133.8, 133.3, 130.0, 129.2, 127.6, 127.34, 127.28, 125.8, 125.6, 124.9, 120.3, 118.7, 111.0, 110.7

HRMS (DART) m/z calcd for C$_{18}$H$_{11}$N$_2$O [MH]$^+$: 271.0871. found 271.0872

Example 37

6-Methyl-2-(naphthalen-2-yl)benzoxazole was obtained in the same manner as in Example 1, except using 6-methylbenzoxazole instead of benzoxazole. The yield thereof was 96%.

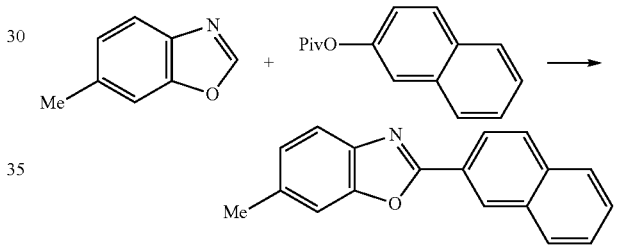

The following is an analytical result of 6-methyl-2-(naphthalen-2-yl)benzoxazole.

$^1$H NMR (400 MHz, CDCl$_3$): δ 8.67 (s, 1H), 8.24 (dd, 1H, J=8.7, 1.4 Hz), 7.95-7.86 (m, 2H), 7.85-7.77 (m, 1H), 7.63 (d, 1H, J=8.2 Hz), 7.54-7.46 (m, 2H), 7.33 (s, 1H), 7.12 (d, 1H, J=8.2 Hz), 2.46 (s, 3H)

$^{13}$C NMR (100 MHz, CDCl$_3$): δ 162.6, 151.0, 139.9, 135.5, 134.5, 132.9, 128.8, 128.6, 127.8, 127.7, 127.5, 126.7, 125.7, 124.5, 123.8, 119.2, 110.7, 21.7

HRMS (DART) m/z calcd for C$_{18}$H$_{14}$NO [MH]$^+$: 260.1075. found 260.1075

Example 38

Texamine was obtained in the same manner as in Example 1, except that 5-(1,3-benzoxazol-5-yl)oxazole was used instead of benzoxazole, and phenyl triflate was used instead of naphthalen-2-yl pivalate. The yield thereof was 62%.

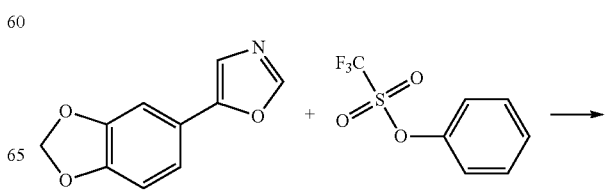

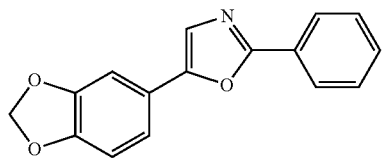

The following is an analytical result of texamine.

$^1$H NMR (400 MHz, CDCl$_3$): δ 8.06 (dd, 2H, J=8.4, 1.6 Hz), 7.50-7.39 (m, 3H), 7.28 (s, 1H), 7.20 (dd, 1H, J=8.0, 1.6 Hz), 7.14 (s, 1H), 6.84 (d, 1H, J=8.0 Hz), 5.97 (s, 2H)

$^{13}$C NMR (100 MHz, CDCl$_3$): δ 160.5, 151.0, 148.1, 147.8, 130.1, 128.7, 127.4, 126.1, 122.3, 122.1, 118.2, 108.7, 104.7, 101.3

HRMS (DART) m/z calcd for C$_{16}$H$_{12}$NO$_3$ [MH]$^+$: 266.0817. found 266.0817

Example 39

Unguenenazole was obtained in the same manner as in Example 1, except that 5-(4-methoxyphenyl)oxazole was used instead of benzoxazole, and phenyl triflate was used instead of naphthalen-2-yl pivalate. The yield thereof was 73%.

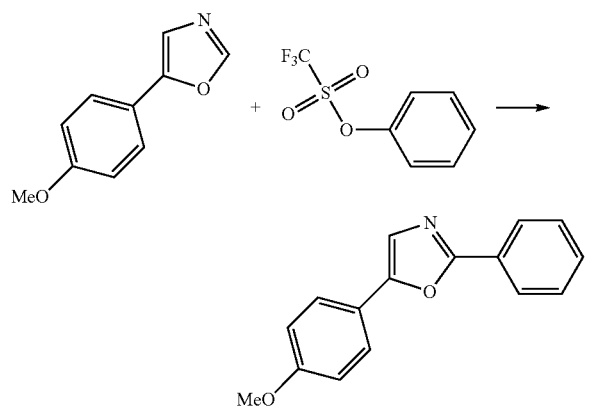

The following is an analytical result of unguenenazole.

$^1$H NMR (400 MHz, CDCl$_3$): δ 8.08 (dd, 2H, J=8.0, 1.8 Hz), 7.62 (dd, 2H, J=9.2, 2.3 Hz), 7.50-7.39 (m, 3H), 7.31 (s, 1H), 6.95 (dd, 2H, J=9.2, 2.3 Hz), 3.83 (s, 3H)

$^{13}$C NMR (100 MHz, CDCl$_3$): δ 160.5, 159.7, 151.2, 130.0, 128.7, 127.5, 126.1, 125.7, 121.9, 120.8, 114.3, 55.3

HRMS (DART) m/z calcd for C$_{16}$H$_{14}$NO$_2$ [MH]$^+$: 252.1025. found 252.1025

Example 40

Ethyl 5-(4-methoxyphenyl)-2-phenyloxazole-4-carboxylate was obtained in the same manner as in Example 1, except that ethyl 5-(4-methoxyphenyl)-1,3-oxazole-4-carboxylate was used instead of benzoxazole, and phenyl triflate was used instead of naphthalen-2-yl pivalate. The yield thereof was 73%.

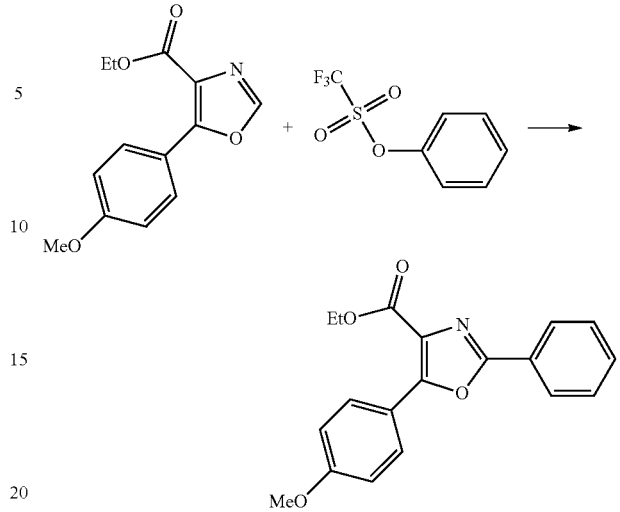

The following is an analytical result of ethyl 5-(4-methoxyphenyl)-2-phenyloxazole-4-carboxylate.

$^1$H NMR (400 MHz, CDCl$_3$): δ 8.17-8.06 (m, 4H), 7.49-7.43 (m, 3H), 7.00 (dd, 2H, J=9.2, 2.4 Hz), 4.45 (q, 2H, J=7.2 Hz), 3.86 (s, 3H), 1.43 (t, 3H, J=7.2 Hz)

$^{13}$C NMR (100 MHz, CDCl$_3$): δ 162.4, 161.0, 159.0, 155.3, 130.7, 130.1, 128.6, 126.9, 126.6, 126.4, 119.5, 113.7, 61.2, 55.3, 14.2

HRMS (DART) m/z calcd for C$_{19}$H$_{18}$NO$_4$ [MH]$^+$: 324.1236. found 324.1236

Example 41

2-(Naphthalen-2-yl)-5-phenylthiazole was obtained in the same manner as in Example 1, except using 5-phenylthiazole triflate instead of benzoxazole. The yield thereof was 64%.

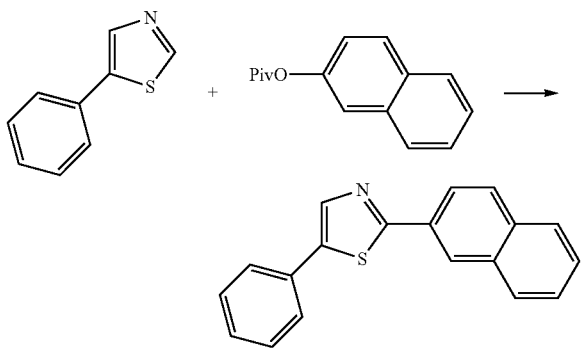

The following is an analytical result of 2-(naphthalen-2-yl)-5-phenylthiazole.

$^1$H NMR (400 MHz, CDCl$_3$): δ 8.42 (s, 1H), 8.09-8.00 (m, 2H), 7.93-7.78 (m, 3H), 7.60 (d, 2H, J=7.8 Hz), 7.52-7.48 (m, 2H), 7.40 (t, 2H, J=7.8 Hz), 7.32 (t, 1H, J=7.3 Hz)

$^{13}$C NMR (100 MHz, CDCl$_3$): δ 167.1, 139.4, 139.3, 134.1, 133.2, 131.4, 131.0, 129.1, 128.7, 128.6, 128.3, 127.8, 127.0, 126.8, 126.6, 125.7, 123.7

HRMS (DART) m/z calcd for C$_{19}$H$_{14}$NS [MH]$^+$: 288.0847. found 288.0846

Example 42

Production of 5-phenyloxazol-2-yl estrone

At room temperature, triethylamine (1.0 mL, 7.2 mmol, 1.2 equiv.) was added to a solution prepared by dissolving estrone (1.62 g, 6.0 mmol) in 10 mL of dichloromethane. The mixture was cooled to 0° C., and then trifluoromethanesulfonyl chloride (760 pt, 7.2 mmol, 1.2 equiv.) was added to the mixture over 3 minutes or more with stirring to effect a reaction. After 6 hours, the reaction was quenched by adding a saturated sodium hydrogen carbonate aqueous solution (10 mL) to the reaction mixture, and the reaction mixture was separated into two layers. The organic layer (dichloromethane solution) was isolated preparatively, and 20 mL of dichloromethane was added to the aqueous layer to extract the product. The above operation was repeated twice. An excess amount of anhydrous magnesium sulfate was added to the collected organic layer (dichloromethane solution), and the mixture was filtered. The solvent was evaporated under reduced pressure to obtain a concentrate including a crude product. The concentrate was subjected to silica gel flash column chromatography (eluant: hexane/ethyl acetate=5/1) to obtain estrone triflate (Rf=0.36, white solid, 1.98 g) (see below). The yield thereof was 82%.

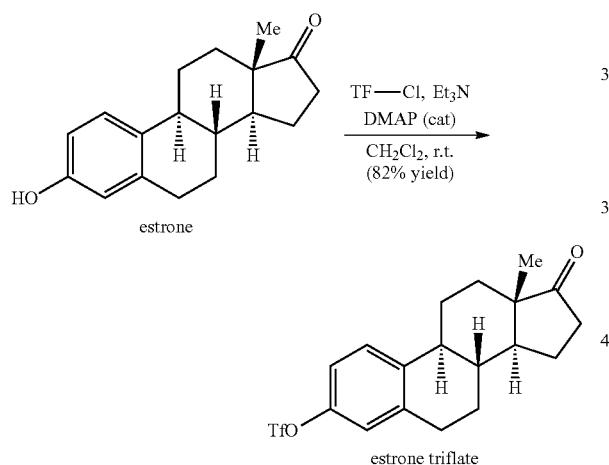

The following is an analytical result of estrone triflate.
$^1$H-NMR (400 MHz, CDCl$_3$): δ 7.34 (d, 1H, J=9.2 Hz), 7.03 (d, 1H, J=8.7 Hz), 6.99 (s, 1H), 3.00-2.90 (m, 2H), 2.52 (ddd, 1H, J=18.8, 9.2, 2.8 Hz), 2.50-2.36 (m, 1H), 2.36-2.25 (m, 1H), 2.24-2.01 (m, 3H), 1.98 (dd, 1H, J=9.6, 2.3 Hz), 1.69-1.44 (m, 6H), 0.92 (s, 3H)

A glass reaction vessel (20 mL, equipped with a J. Young (registered trademark) O-ring tap) charged with magnetic stir bars and cesium carbonate (195.5 mg, 0.60 mmol, 1.5 equiv.) was dried under reduced pressure using a heat gun, cooled to room temperature, and filled with argon gas. After the addition of 5-phenyloxazole (58.0 mg, 0.40 mmol) and estrone triflate (241.5 mg, 0.60 mmol, 1.5 equiv.), the reaction vessel was placed in a glovebox filled with argon gas.

Ni(cod)$_2$ (11.2 mg, 0.04 mmol, 10 mol %) and 1,2-bis(dicyclohexylphosphino)ethane (33.8 mg, 0.08 mmol, 20 mol %) were added to the reaction vessel. After removing the reaction vessel from the glovebox, 1.6 mL of 1,4-dioxane was added to the reaction vessel under an argon gas stream. After sealing the reaction vessel with the O-ring tap, the mixture was reacted at 120° C. for 24 hours with stirring. The reaction mixture was then cooled to room temperature, and subjected to column chromatography (eluant: ethyl acetate) using a short pad of silica gel. The filtrate was concentrated, and the concentrate was subjected to thin-layer chromatography (eluant: chloroform) to obtain 5-phenyloxazol-2-yl estrone (Rf=0.5, white solid, 83.3 mg) (see below). The yield thereof was 52%.

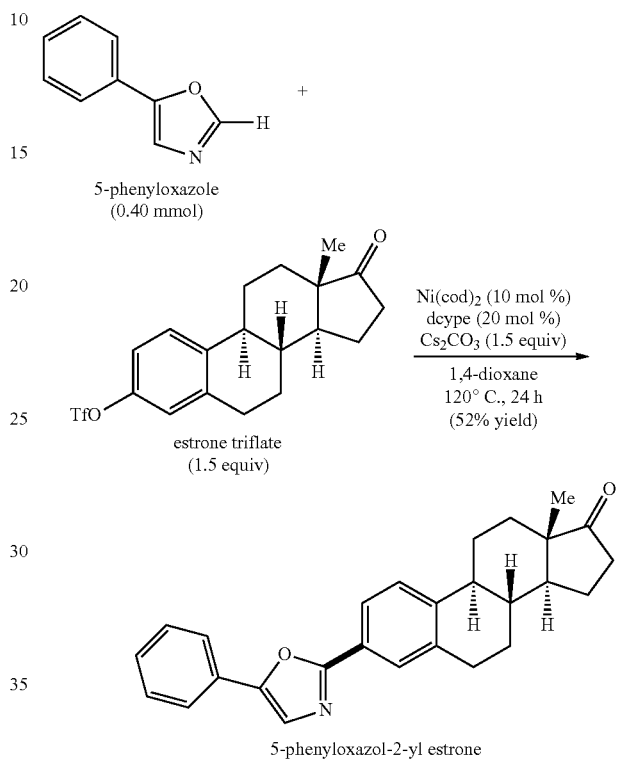

The following is an analytical result of 5-phenyloxazol-2-yl estrone.
$^1$H-NMR (400 MHz, CDCl$_3$): δ 7.87-7.79 (m, 2H), 7.70 (d, 2H, J=7.6 Hz), 7.46-7.39 (m, 3H), 7.38-7.29 (m, 2H), 3.01-2.92 (m, 2H), 2.50 (d, 1H, J=18.8, 8.8 Hz), 2.44-2.38 (m, 1H), 2.33-2.25 (m, 1H), 2.18-1.94 (m, 4H), 1.68-1.39 (m, 6H), 0.91 (s, 3H)
$^{13}$C NMR (100 MHz, CDCl$_3$): δ 220.5, 161.2, 150.8, 142.3, 137.0, 128.8, 128.2, 127.9, 126.6, 125.7, 124.8, 124.0, 123.5, 123.2, 50.3, 47.8, 44.4, 37.7, 35.7, 31.4, 29.2, 26.2, 25.5, 21.4, 13.7
HRMS (DART) m/z calcd for $C_{27}H_{28}NO_2$ [MH]$^+$: 398.2120. found 398.2119

Example 43

Production of benzoxazol-2-yl quinine

A two-necked flask (internal volume: 100 mL) charged with magnetic stir bars was dried under reduced pressure using a heat gun, cooled to room temperature, and filled with argon gas. After the addition of quinine (1.33 g, 4.1 mmol) and sodium ethanethiolate (1.38 g, 16.4 mmol, 4.0 equiv.) to the flask, 30 mL of dimethylformamide was added to the mixture. The mixture was heated at 120° C. for 12 hours using an oil bath. After cooling the reaction mixture to room temperature, the reaction was quenched by adding a saturated ammonium chloride aqueous solution (30 mL), and the reaction mixture was separated into two layers. The organic layer (dimethylformamide solution) was isolated preparatively, and 25 mL of ethyl acetate was added to the aqueous layer to extract the product. The above operation was repeated four times. An excess amount of anhydrous magnesium sulfate was added to the collected organic layer (mixture of dimethylformamide solution and ethyl acetate solution), and the mixture was filtered. The solvent was evaporated under reduced pressure to obtain a concentrate including a crude product. The concentrate was washed with hexane including dichloromethane (10%) to obtain demethylated quinine (quinine-OH) (white solid, 1.27 g) (see below). The yield thereof was 99%.

A two-necked flask (internal volume: 30 mL) charged with magnetic stir bars was charged with demethylated quinine (quinine-OH) (465.6 mg, 1.5 mmol). The flask was cooled to 0° C., triethylamine (238 μL, 1.1 equiv.), dichloromethane (3.0 mL), and trifluoromethanesulfonyl chloride (166 μL, 1.05 equiv.) were added to the flask, and the mixture was reacted at room temperature with stirring. After 8 hours, the reaction was quenched by adding a saturated sodium hydrogen carbonate aqueous solution (5 mL) to the reaction mixture, and the reaction mixture was separated into two layers. The organic layer (dichloromethane solution) was isolated preparatively, and 15 mL of dichloromethane was added to the aqueous layer to extract the product. The above operation was repeated four times. An excess amount of anhydrous magnesium sulfate was added to the collected organic layer (dichloromethane solution), and the mixture was filtered. The solvent was evaporated under reduced pressure to obtain a concentrate including a crude product. The concentrate was sequentially subjected to silica gel flash column chromatography (eluant: chloroform/methanol=9/1, Rf=0.26)) and reversed-phase high-performance liquid chromatography (eluant: water and acetonitrile (gradient)) to obtain quinine triflate (white solid, 265.9 mg) (see below). The yield thereof was 40%.

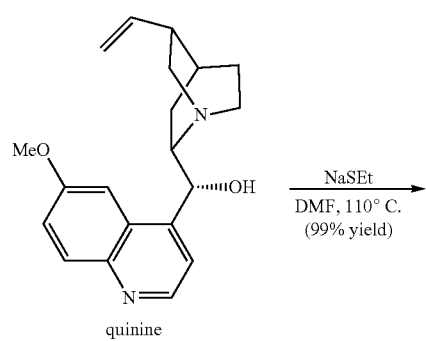

quinine

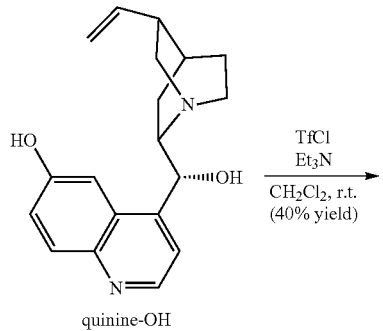

quinine-OH

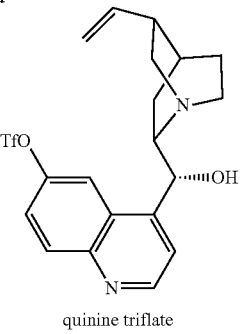

quinine triflate

The following is an analytical result of demethylated quinine (quinine-OH).

$^1$H-NMR (400 MHz, CD$_3$OD): δ 8.60 (d, 1H, J=4.8 Hz), 7.91 (d, 1H, J=9.2 Hz), 7.63 (d, 1H, J=4.4 Hz), 7.34 (dd, 1H, J=9.2, 2.8 Hz), 7.29 (d, 1H, J=2.4 Hz), 5.81-5.69 (m, 1H), 5.57 (d, 1H, J=2.8 Hz), 5.03-4.89 (m, 1H), 4.88-4.83 (m, 1H), 3.78 (br, 1H), 3.24-3.12 (m, 2H), 2.86-2.72 (m, 2H), 2.43 (br, 1H), 1.97-1.86 (m, 2H), 1.84 (br, 1H), 1.65 (br, 1H), 1.51-1.41 (m, 1H)

The following is an analytical result of quinine triflate.

$^1$H-NMR (400 MHz, CD$_3$OD): δ 8.91 (d, 1H, J=4.4 Hz), 8.36 (d, 1H, J=2.4 Hz), 8.20 (d, 1H, J=9.6 Hz), 7.77-7.71 (m, 2H), 5.82-5.71 (m, 1H), 5.45 (d, 1H, J=4.8 Hz), 5.01-4.85 (m, 2H), 3.58-3.46 (br, 1H), 3.20-3.12 (br, 1H), 3.05 (dd, 1H, J=14.0, 10.8 Hz), 2.71-2.60 (m, 2H), 2.39-2.29 (br, 1H), 1.89-1.78 (m, 3H), 1.68-1.52 (m, 2H)

$^{13}$C NMR (100 MHz, CD$_3$OD): δ 153.9, 149.9, 149.3, 144.0, 134.5, 128.8, 125.5, 123.0, 121.6 (q, JC-F=322.0 Hz), 119.2, 116.3, 74.6, 63.2, 58.6, 45.0, 42.1, 30.4, 29.5, 24.5

Subsequently, a glass reaction vessel (20 mL, equipped with a J. Young (registered trademark) O-ring tap) charged with magnetic stir bars and cesium carbonate (122.2 mg, 0.375 mmol, 1.5 equiv.) was dried under reduced pressure using a heat gun, cooled to room temperature, and filled with argon gas. After the addition of quinine triflate (165.9 mg, 0.375 mmol, 1.5 equiv.), the reaction vessel was placed in a glovebox filled with argon gas.

After that, Ni(cod)$_2$ (7.0 mg, 0.025 mmol, 10 mol %) and 1,2-bis(dicyclohexylphosphino)ethane (20.8 mg, 0.05 mmol, 20 mol %) were added to the reaction vessel. The reaction vessel was removed from the glovebox, and benzoxazole (29.8 mg, 0.25 mmol, 1.0 equiv.) and 1,4-dioxane (1.0 mL) were added to the reaction vessel under an argon gas stream. After sealing the reaction vessel with the O-ring tap, the mixture was reacted at 120° C. for 24 hours with stirring. The reaction mixture was then cooled to room temperature, and subjected to column chromatography (eluant: ethyl acetate) using a short pad of silica gel. The filtrate was concentrated, and the concentrate was sequentially subjected to thin-layer chromatography (eluant: chloroform/methanol=10/1, Rf=0.17)) and reversed-phase high-performance liquid chromatography (eluant: water and acetonitrile (gradient)) to obtain benzoxazol-2-yl quinine (white solid, 43.9 mg) (see below). The yield thereof was 43%.

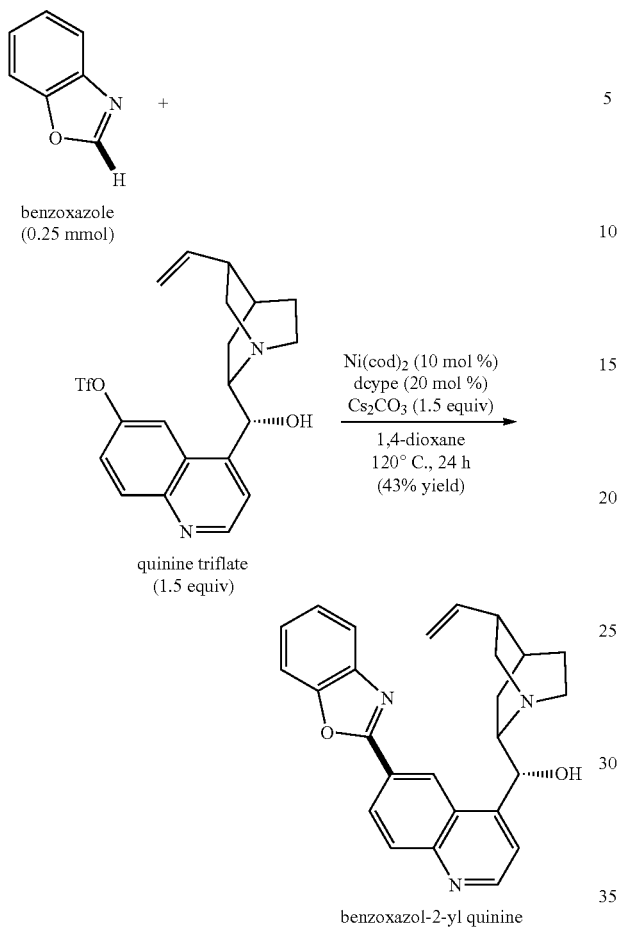

benzoxazole (0.25 mmol)

quinine triflate (1.5 equiv)

Ni(cod)₂ (10 mol %)
dcype (20 mol %)
Cs₂CO₃ (1.5 equiv)
1,4-dioxane
120° C., 24 h
(43% yield)

benzoxazol-2-yl quinine

The following is an analytical result of benzoxazol-2-yl quinine.

$^{1}$H-NMR (400 MHz, CDCl$_3$): δ 8.55 (s, 1H), 8.28 (d, 1H, J=4.4 Hz), 8.08 (dd, 1H, J=8.8, 1.2 Hz), 7.93 (d, 1H, J=8.8 Hz), 7.72-7.65 (m, 1H), 7.64-7.57 (m, 1H), 7.44 (d, 1H, J=4.4 Hz), 7.42-7.35 (m, 2H), 5.82 (d, 1H, J=2.8 Hz), 5.72-5.61 (m, 1H), 4.96-4.82 (m, 2H), 3.73-3.58 (m, 1H), 3.13 (dd, 1H, J=14.0, 10.4 Hz), 3.04-2.94 (m, 1H), 2.82-2.68 (m, 1H), 2.60 (dd, 1H, J=14.0, 3.2 Hz), 2.30 (br, 1H), 2.00-1.85 (m, 2H), 1.85-1.79 (m, 1H), 1.62-1.49 (m, 1H), 1.48-1.38 (m, 1H)

$^{13}$C NMR (100 MHz, CDCl$_3$): δ 161.9, 151.3, 150.7, 150.6, 148.7, 141.4, 141.3, 130.7, 126.4, 125.5, 124.9, 124.8, 123.9, 122.8, 119.8, 118.8, 114.4, 110.9, 70.5, 60.7, 56.4, 42.9, 39.6, 27.9, 27.1, 20.4

HRMS (DART) m/z calcd for $C_{26}H_{26}N_3O_2$ [MH]$^+$: 412.2025. found 412.2025

INDUSTRIAL APPLICABILITY

Since the method according to the present invention can produce a compound in which the carbon atom indicated by * in the general formula (2) and the carbon atom indicated by * in the general formula (3) are bonded to each other (see the above reaction scheme), a wide range of heteroaromatic compounds and phenol derivatives can be selectively used, and a compound having the target structure can be inexpensively and efficiently obtained. Therefore, a compound having the target structure (e.g., a biologically active compound, drug (e.g., compound having a steroid skeleton or an alkaloid skeleton), an organic electronic material, or an intermediate thereof) can be easily produced by utilizing the desired atom or functional group as a substituent that substitutes the heteroaromatic compound or the phenol derivative.

The invention claimed is:

1. A method for producing a heterocyclic compound represented by a general formula (1), the method comprising reacting a heteroaromatic compound represented by a general formula (2) with a phenol derivative represented by a general formula (3) in the presence of a nickel compound, 1,2-bis(dicyclohexylphosphino)ethane, and a base, wherein the nickel compound is bis(1,5-cyclooctadiene)nickel(0),

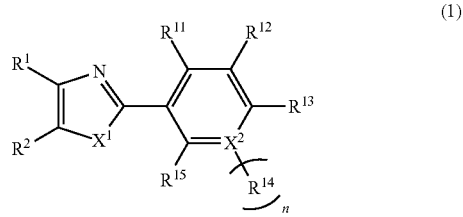

(1)

wherein in formula (1):

$X^1$ is an oxygen atom or a sulfur atom, $X^2$ is a carbon atom or a nitrogen atom, n is 0 when $X^2$ is a nitrogen atom, and is 1 when $X^2$ is a carbon atom, $R^1$ is a hydrogen atom, a hydrocarbon group having 1 to 20 carbon atoms, a group derived therefrom, or an ester group, $R^2$ is a hydrogen atom, a hydrocarbon group having 1 to 20 carbon atoms, a group derived therefrom, or an ester group, provided that $R^1$ and $R^2$ optionally bond to each other to form a divalent organic group having 4 to 6 carbon atoms, $R^{11}$ is a hydrogen atom, a hydrocarbon group having 1 to 20 carbon atoms, a group derived therefrom, or an alkoxy group having 1 to 10 carbon atoms, $R^{12}$ is a hydrogen atom, a hydrocarbon group having 1 to 20 carbon atoms, a group derived therefrom, or an alkoxy group having 1 to 10 carbon atoms, $R^{13}$ is a hydrogen atom, a hydrocarbon group having 1 to 20 carbon atoms, a group derived therefrom, or an alkoxy group having 1 to 10 carbon atoms, $R^{14}$ is a hydrogen atom, a hydrocarbon group having 1 to 20 carbon atoms, a group derived therefrom, or an alkoxy group having 1 to 10 carbon atoms, and $R^{15}$ is a hydrogen atom, a hydrocarbon group having 1 to 20 carbon atoms, a group derived therefrom, or an alkoxy group having 1 to 10 carbon atoms, provided that $R^{11}$ and $R^{12}$ optionally bond to each other to form a divalent organic group having 4 to 6 carbon atoms, $R^{12}$ and $R^{13}$ optionally bond to each other to form a divalent organic group having 4 to 6 carbon atoms, $R^{13}$ and $R^{14}$ optionally bond to each other to form a divalent organic group having 4 to 6 carbon atoms, and $R^{14}$ and $R^{15}$ optionally bond to each other to form a divalent organic group having 4 to 6 carbon atoms, (2)

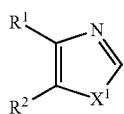

wherein in formula (2):
$X^1$ is an oxygen atom or a sulfur atom,
$R^1$ is a hydrogen atom, a hydrocarbon group having 1 to 20 carbon atoms, a group derived therefrom, or an ester group,
$R^2$ is a hydrogen atom, a hydrocarbon group having 1 to 20 carbon atoms, a group derived therefrom, or an ester group, provided that $R^1$ and $R^2$ optionally bond to each other to form a divalent organic group having 4 to 6 carbon atoms, (3)

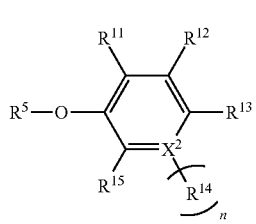

wherein in formula (3):
$X^2$ is a carbon atom or a nitrogen atom,
n is 0 when $X^2$ is a nitrogen atom, and is 1 when $X^2$ is a carbon atom,
$R^5$ is an acyl group, a dialkylcarbamoyl group, an alkyl carbonate group, an aryl carbonate group, an aralkyl carbonate group, a triflate group, an alkylsulfonyl group, an arylsulfonyl group, an aralkylsulfonyl group, a dialkylsulfamoyl group, or a diarylsulfamoyl group,
$R^{11}$ is a hydrogen atom, a hydrocarbon group having 1 to 20 carbon atoms, a group derived therefrom, or an alkoxy group having 1 to 10 carbon atoms,
$R^{12}$ is a hydrogen atom, a hydrocarbon group having 1 to 20 carbon atoms, a group derived therefrom, or an alkoxy group having 1 to 10 carbon atoms,
$R^{13}$ is a hydrogen atom, a hydrocarbon group having 1 to 20 carbon atoms, a group derived therefrom, or an alkoxy group having 1 to 10 carbon atoms,
$R^{14}$ is a hydrogen atom, a hydrocarbon group having 1 to 20 carbon atoms, a group derived therefrom, or an alkoxy group having 1 to 10 carbon atoms, and
$R^{15}$ is a hydrogen atom, a hydrocarbon group having 1 to 20 carbon atoms, a group derived therefrom, or an alkoxy group having 1 to 10 carbon atoms,
provided that $R^{11}$ and $R^{12}$ optionally bond to each other to form a divalent organic group having 4 to 6 carbon atoms, $R^{12}$ and $R^{13}$ optionally bond to each other to form a divalent organic group having 4 to 6 carbon atoms, $R^{13}$ and $R^{14}$ optionally bond to each other to form a divalent organic group having 4 to 6 carbon atoms, and $R^{14}$ and $R^{15}$ optionally bond to each other to form a divalent organic group having 4 to 6 carbon atoms.

2. The method according to claim 1, wherein the heteroaromatic compound represented by the general formula (2) is an oxazole derivative, a benzoxazole derivative, or a benzothiazole derivative.

3. The method according to claim 1, wherein the phenol derivative represented by the general formula (3) is a compound having a formula selected from the group consisting of general formulae (3-1) to (3-16), (3-1)
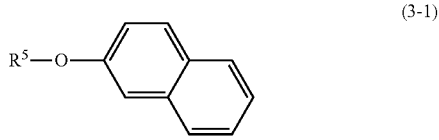

(3-2)
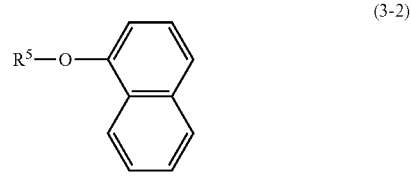

(3-3)
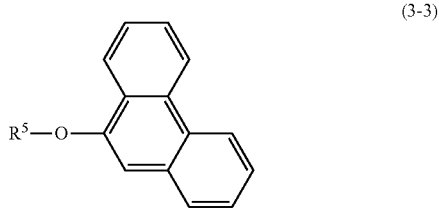

(3-4)
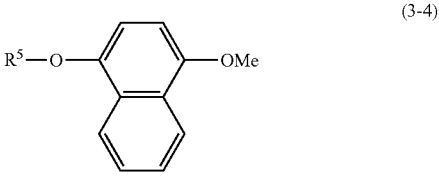

(3-5)
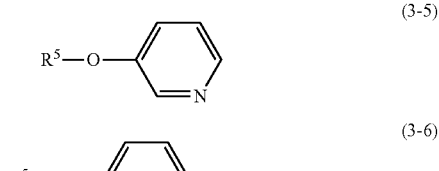

(3-6)
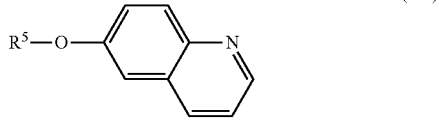

(3-7)
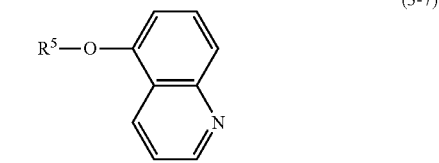

(3-8)
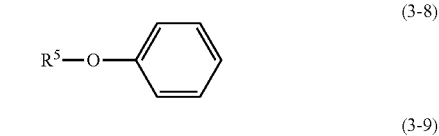

(3-9)
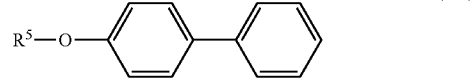

(3-10)
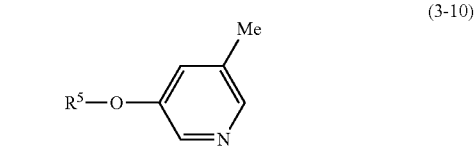

-continued

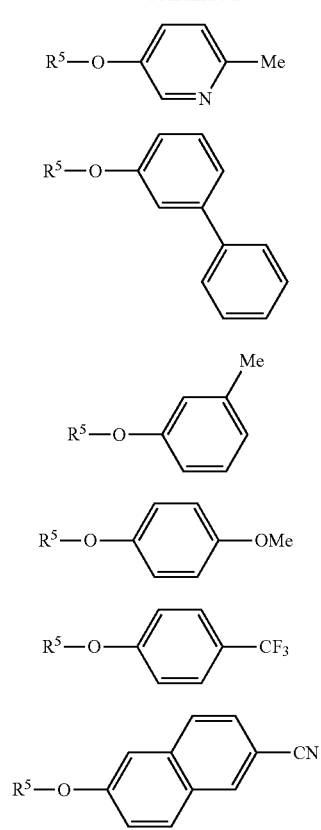

(3-11)
(3-12)
(3-13)
(3-14)
(3-15)
(3-16)

wherein $R^5$ is an acyl group, a dialkylcarbamoyl group, an alkyl carbonate group, an aryl carbonate group, an aralkyl carbonate group, a triflate group, an alkylsulfonyl group, an arylsulfonyl group, an aralkylsulfonyl group, a dialkylsulfamoyl group, or a diarylsulfamoyl group.

4. The method according to claim 1, wherein $R^5$ is a pivaloyl group, a dimethylcarbamoyl group, a triflate group, or a methanesulfonyl group.

5. The method according to claim 1, wherein a molar ratio of Ni atoms included in the nickel compound to 1,2-bis(dicyclohexylphosphino)ethane is in a range of 1:1.2 to 1:3.

6. The method according to claim 1, wherein the nickel compound is present in an amount of 0.05 to 0.1 mol based on 1 1 mol of the heteroaromatic compound.

7. The method according to claim 1, wherein the 1,2-bis(dicyclohexylphosphino)ethane is present in an amount of 0.1 to 0.2 mol based on 1 mol of the heteroaromatic compound.

8. The method according to claim 1, wherein a base is present during the reacting.

9. The method according to claim 8, wherein the base is at least one compound selected from the group consisting of lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate, potassium acetate, a lithium salt of an alkoxide having 1 to 6 carbon atoms, a sodium salt of an alkoxide having 1 to 6 carbon atoms, a potassium salt of an alkoxide having 1 to 6 carbon atoms, a lithium salt of an alkyl anion having 1 to 6 carbon atoms, a sodium salt of an alkyl anion having 1 to 6 carbon atoms, a potassium salt of an alkyl anion having 1 to 6 carbon atoms, diisopropylethylamine, tributylamine, N-methylmorpholine, diazabicycloundecene, diazabicyclooctane, and imidazole.

* * * * *